(12) United States Patent
Luo

(10) Patent No.: US 10,040,835 B2
(45) Date of Patent: *Aug. 7, 2018

(54) VECTORS ENCODING ROD-DERIVED CONE VIABILITY FACTOR

(71) Applicant: Wellstat Ophthalmics Corporation, Gaithersburg, MD (US)

(72) Inventor: Tianci Luo, Clarksville, MD (US)

(73) Assignee: Wellstat Ophthalmics Corporation, Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/962,337

(22) Filed: Dec. 8, 2015

(65) Prior Publication Data

US 2016/0108099 A1    Apr. 21, 2016

Related U.S. Application Data

(63) Continuation of application No. 14/354,415, filed as application No. PCT/US2012/062106 on Oct. 26, 2012, now Pat. No. 9,265,813.

(Continued)

(51) Int. Cl.
| | |
|---|---|
| *C12N 15/62* | (2006.01) |
| *C12N 15/86* | (2006.01) |
| *C12Q 1/68* | (2018.01) |
| *C07K 14/47* | (2006.01) |
| *A61K 38/44* | (2006.01) |

(Continued)

(52) U.S. Cl.
CPC .............. *C07K 14/47* (2013.01); *A61K 38/44* (2013.01); *C12N 9/0004* (2013.01); *C12N 9/0051* (2013.01); *C12N 15/86* (2013.01); *A61K 38/00* (2013.01); *A61K 48/0066* (2013.01); *C07K 2319/02* (2013.01);

(Continued)

(58) Field of Classification Search
None
See application file for complete search history.

(56) References Cited

U.S. PATENT DOCUMENTS

| 8,071,745 B2 | 12/2011 | Leveillard |
| 8,114,849 B2 | 2/2012 | Leveillard |

(Continued)

FOREIGN PATENT DOCUMENTS

| RU | 2345780 C2 | 2/2009 |
| WO | 2002081513 A2 | 10/2002 |

(Continued)

OTHER PUBLICATIONS

Yang et al., "Functional cone rescue by RdCVF protein in a dominant model of retinitis pigmentosa" Molecular Therapy (2009). 17(5): 787-795.

(Continued)

*Primary Examiner* — Adam Weidner
*Assistant Examiner* — Aurora M Fontainhas
(74) *Attorney, Agent, or Firm* — Lewis J. Kreisler

(57) ABSTRACT

The present invention relates to nucleic acids coding for and capable of expressing a rod-derived cone viability factor (RdCVF) and viral vectors containing these nucleic acids. The invention also relates to compositions and pharmaceutical preparations comprising these nucleic acids or vectors, methods of producing or secreting an RdCVF, and methods of treatment.

26 Claims, 9 Drawing Sheets

Related U.S. Application Data

(60) Provisional application No. 61/552,155, filed on Oct. 27, 2011.

(51) Int. Cl.
*C12N 9/02* (2006.01)
*A61K 48/00* (2006.01)
*A61K 38/00* (2006.01)

(52) U.S. Cl.
CPC ............ *C12N 2750/14143* (2013.01); *C12N 2799/025* (2013.01); *C12N 2800/22* (2013.01); *C12N 2830/42* (2013.01)

(56) References Cited

U.S. PATENT DOCUMENTS

| | | |
|---|---|---|
| 8,394,756 B2 | 3/2013 | Leveillard |
| 8,518,695 B2 | 8/2013 | Leveillard |
| 2003/0018984 A1 | 1/2003 | Coleman et al. |
| 2005/0191747 A1 | 9/2005 | Luo et al. |
| 2007/0141557 A1 | 6/2007 | Raab et al. |
| 2009/0215679 A1 | 8/2009 | Leveillard et al. |
| 2010/0247496 A1 | 9/2010 | Leveillard et al. |
| 2011/0034546 A1 | 2/2011 | O'Riordan |
| 2012/0034546 A1 | 4/2012 | Inoue et al. |
| 2012/0108657 A1 | 5/2012 | Leveillard |
| 2012/0245093 A1 | 9/2012 | Leveillard |

FOREIGN PATENT DOCUMENTS

| | | | |
|---|---|---|---|
| WO | 2004098499 A2 | 11/2004 | |
| WO | WO2009/146183 | * 12/2009 | ............ C12N 15/64 |
| WO | 2010029130 A1 | 3/2010 | |
| WO | 2010050586 A1 | 5/2010 | |

OTHER PUBLICATIONS

Leveillard et al., "Identification and characterization of rod-derived cone viability factor" Nature Genetics (2004). 366(7): 755-759.

Byrne et al., "AAV-mediated deliver of rod-derived cone viability factor in a mouse model of retinal degeneration" Annual Meeting of the Association for Research in Vision and Ophthalmology (May 2, 2011). Presentation Abstract. Session 228, Program No. 1395.

Fridlich et al., "The thioredoxin-like protein rod-derived cone viability factor (RdCVFL) interacts with TAU and inhibits its phosphorylation in the retina" Molecular & Cellular Proteomics (2009). 8(6): 1206-1218.

Wang et al., "Thioredoxin-like 6 protects retinal cell line from photooxidative damage by upregulating NF-kappaB activity" Free Radical Biology & Medicine (2008). 45(3): 336-344.

Fath et al., "Multiparameter RNA and codon optimization: a standardized tool to assess and enhance autologous mammalian gene expression" PLoS One (Mar. 3, 2011). 6(3): e17596, 14 pages.

McClements et al., "Gene therapy for retinal disease" Translational Research (2013). 161(4): 241-254.

Hoover, et al., "DNAWorks: an automated method for designing oligonucleotides for PCR-based gene synthesis", Nucleic Acids Research, 2002, vol. 30, No. 10 e43.

GenBank submission NM_138454. Mar. 2015 [online]. [Retrieved on Jul. 6, 2015]. Retrieved from the internet: <URL:http://www.ncbi.nlm.nih.gov/nucleotide/NM_138454.1>.

Sahel, et al., "Rod-cone interdependence: implications for therapy of photoreceptor cell diseases" in Prog. Brain Res., Kolb, et al., eds., vol. 131, Ch. 47, pp. 649-661, 2001.

Mohand-Said, et al., "Rod-Cone Interactions: Developmental and Clinical Significance", Prog. Retinal and Eye Res. 20 (4): 451-467, 2001.

Leveillard, et al., "Rod-derived cone viability factor for treating blinding diseases: from clinic to redox signaling", Sci Transl Med. Apr. 2010 ; 2(26): 26ps16. doi:10.1126/scitranslmed.3000866.

Cronin, et al., "The disruption of the rod-derived cone viability gene leads to photoreceptor dysfunction and susceptibility to oxidative stress", Cell Death Differ. Jul. 2010 ; 17(7): 1199-1210. doi:10.1038/cdd.2010.2.

Graf, et al., "Concerted Action of Multiple cis-Acting Sequences is Required for Rev Dependence of Late Human Immunodeficiency Virus Type 1 Gene Expression", J. Virol., Nov. 2000, vol. 74, No. 22, pp. 10822-10826.

Plotkin, et al., "Synonymous but not the same: the causes and consequences of codon bias", Nat Ref Genet. Jan. 2011 ; 12(1): 32-42. doi:10.1038/nrg2899.

Angov, "Codon usage: Nature's roadmap to expression and folding of proteins", Biotechnol. J. 2011, 6, 650-659. DOI 10.1002/BIOT.201000332.

Rocha, "Codon usage bias from tRNA's point of view: Redundancy, specialization, and efficient decoding for translation optimization", Genome Research, 2004, 14:2279-2286.

Defne Audrey Amado, "Gene Therapy in the Retina: Exploring Neurotrophic Treatment and AAV Readministration in Retinal Disease" (PhD dissertation, U. Pennsylvania 2010).

Chalmel, et al., "Rod-derived Cone Viability Factor-2 is a novel bifunctional-thioredoxin-like protein with therapeutic potential", BMC Molecular Biology 2007, 8:74. doi:10.1186/1471-2199-8-74. <URL:http://www.biomedcentral.com/1471-2199/8/74>.

Jaillard et al., "Impaired vision and olfaction in mice lacking RdCVF2", ARVO Annual Meeting Abstract, Investigative Ophthalmology & Visual Science 50(13):491. Apr. 2009.

Wang et al., "Neuroprotective effect of protective inoculation of optimized ha-syn genetic vaccine on mice sufferinng from MPTP-induced acute Parkinson's disease", Third Military Medical University Journals. 31(18). Sep. 30, 2009.

Andrews et al., "Sequences beyond the cleavage site influence signal peptide function", J. Biol. Chem. 263(30): 15791-15798. Oct. 25, 1988.

Choo et al., "Flanking signal and mature peptide residues influence signal peptide cleavage", BMC Bioinformatics. 9 (Suppl 12):S15, 11 pages. Dec. 12, 2008. <doi:10.1186/1471-2105-9-S12-S15>.

* cited by examiner

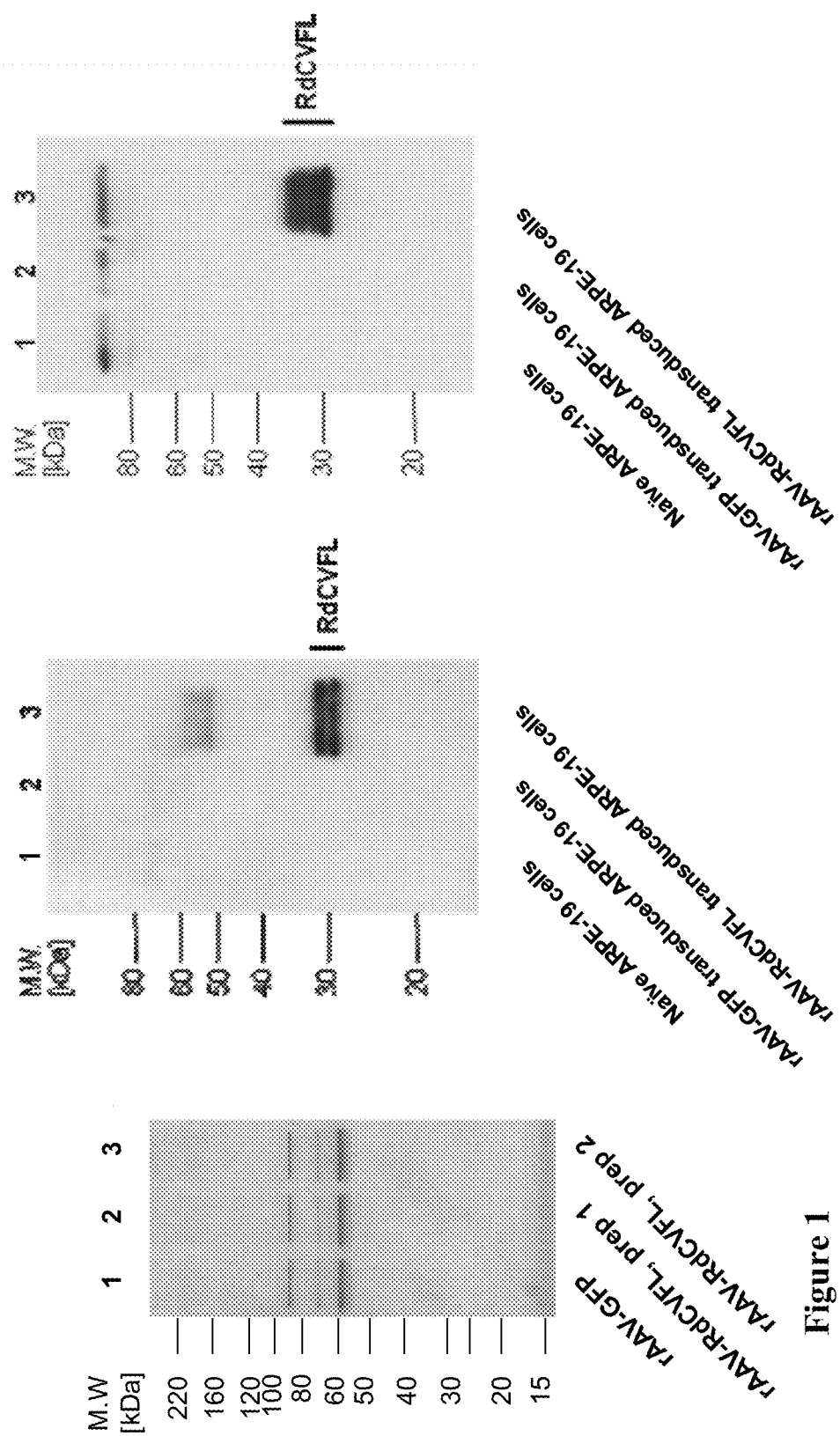

```
rAAV-RdCVF1L        2788 bp    DNA        linear
REFERENCE   1  (bases 1 to 2788)
FEATURES             Location/Qualifiers
     misc_feature    1..141
                     /gene="ITR"
                     /product="AAV left ITR"
                     /SECDrawAs="Region"
     CDS             150..812
                     /gene="CMV Promoter"
                     /product="CMV Promoter"
                     /SECDrawAs="Gene"
     CDS             820..1312
                     /gene="Intron"
                     /product="Human beta-globin intron"
                     /SECDrawAs="Gene"
     misc_feature    1319..1326
                     /gene="MCS"
                     /product="multiple cloning site"
                     /SECDrawAs="Region"
     CDS             1340..2080
                     /gene="IgG-k RdCVFL"
                     /product="IgG-k plus RdCVFL"
                     /SECDrawAs="Gene"
     misc_feature    2085..2129
                     /gene="MCS"
                     /product="multiple cloning site"
                     /SECDrawAs="Region"
     misc_feature    2130..2608
                     /gene="PolyA"
                     /product="PolyA"
                     /SECDrawAs="Region"
     misc_feature    2648..2788
                     /gene="ITR"
                     /product="AAV right ITR"
                     /SECDrawAs="Region"
ORIGIN
    1 cctgcaggca gctgcgcgct cgctcgctca ctgaggccgc ccgggcaaag cccgggcgtc
   61 gggcgacctt tggtcgcccg gcctcagtga gcgagcgagc gcgcagagag ggagtggcca
  121 actccatcac tagggttcc tgcggccgca cgcgtggagc tagttattaa tagtaatcaa
  181 ttacggggtc attagttcat agcccatata tggagttccg cgttacataa cttacggtaa
  241 atggcccgcc tggctgaccg cccaacgacc cccgcccatt gacgtcaata atgacgtatg
  301 ttcccatagt aacgtcaata gggactttcc attgacgtca atgggtggag tatttacggt
  361 aaactgccca cttggcagta catcaagtgt atcatatgcc aagtacgccc cctattgacg
```

Figure 9

```
 421 tcaatgacgg taaatggccc gcctggcatt atgcccagta catgacctta tgggactttc
 481 ctacttggca gtacatctac gtattagtca tcgctattac catggtgatg cggttttggc
 541 agtacatcaa tgggcgtgga tagcggtttg actcacgggg atttccaagt ctccacccca
 601 ttgacgtcaa tgggagtttg ttttgcacca aaatcaacgg gactttccaa aatgtcgtaa
 661 caactccgcc ccattgacgc aaatgggcgg taggcgtgta cggtgggagg tctatataag
 721 cagagctcgt ttagtgaacc gtcagatcgc ctggagacgc catccacgct gttttgacct
 781 ccatagaaga caccgggacc gatccagcct ccgcggattc gaatcccggc cgggaacggt
 841 gcattggaac gcggattccc cgtgccaaga gtgacgtaag taccgcctat agagtctata
 901 ggcccacaaa aaatgctttc ttcttttaat atactttttt gtttatctta tttctaatac
 961 tttccctaat ctctttcttt cagggcaata atgatacaat gtatcatgcc tctttgcacc
1021 attctaaaga ataacagtga taatttctgg gttaaggcaa tagcaatatt tctgcatata
1081 aatatttctg catataaatt gtaactgatg taagaggttt catattgcta atagcagcta
1141 caatccagct accattctgc ttttatttta tggttgggat aaggctggat tattctgagt
1201 ccaagctagg ccttttgct aatcatgttc atacctctta tcttcctccc acagctcctg
1261 ggcaacgtgc tggtctgtgt gctggcccat cactttggca aagaattggg attcgaacat
1321 cgattgaatt cgagccacca tggagacaga cactcctg ctatgggtac tgctgctctg
1381 ggttccaggt tccactggtg acgcggccca gcggccagg cgcgcgtac gaagcttggt
1441 acccgccagc ctgttcagcg gcggatcct gatcaggaac aacagcgacc aggacgagct
1501 ggacaccgag gccgaagtga caggaggct ggagaacaga ctggtgctgc tgttctttgg
1561 cgccggagcc tgcctcagt gccaggcctt cgtgccatc ctgaaggatt tctttgtgag
1621 gctgaccgac gagttctacg tgctgagagc cgccagctg gccctggtgt atgtgagcca
1681 ggacagcacc gaggagcagc aggacctgtt cctgaaggac atgcccaaga agtggctgtt
1741 cctgcccttc gaggacgacc tgagaagaga cctgggcagg cagttcagcg tggagagact
1801 gcccgccgtg gtggtgctga agcctgatgg cgacgtgctg accagagatg gcgccgacga
1861 gatccagaga ctgggcaccg cctgcttcgc caactggcag gaggccgccg aggtcctgga
1921 cagaaacttc cagctgcccg aggatctgga ggatcaggag cccagatccc tgaccgagtg
1981 cctgaggcgg cacaagtaca gagtggagaa ggccgccaga ggcggcagag accctggcgg
2041 cggaggagga gaggagggcg gagccggcgg actgttctga tgagctagca ccggttgtac
2101 aagtcaagcg gccaaccctc cctagatcta cgggtggcat ccctgtgacc cctccccagt
2161 gcctctcctg gccctggaag ttgccactcc agtgcccacc agccttgtcc taataaaatt
2221 aagttgcatc attttgtctg actaggtgtc cttctataat attatggggt ggaggggggt
2281 ggtatggagc aagggccaag ttggaagaca acctgtagg gcctgcgggg tctattggga
2341 accaagctgg agtgcagtgg cacaatcttg gctcactgca atctccgcct cctgggttca
2401 agcgattctc ctgcctcagc ctcccgagtt gttgggattc caggcatgca tgaccaggct
2461 cagctaattt ttgttttttt ggtagagacg gggtttcacc atattggcca ggctggtctc
2521 caactcctaa tctcaggtga tctacccacc ttggcctccc aaattgctgg gattacaggc
2581 gtgaaccact gctcccttcc ctgtccttct gattttgtag gtaaccacgt gcggaccgag
2641 cggccgcagg aacccctagt gatggagttg gccactccct ctctcgcgcg tcgctcgctc
2701 actgaggccg ggcgaccaaa ggtcgcccga cgcccgggct tgcccgggc ggcctcagtg
2761 agcgagcgag cgcgcagctg cctgcagg  (SEQ ID NO:11)
//
```

ERG Responses of 5-wk old Rd10 mice treated with AAV-RdCVFL

VECTORS ENCODING ROD-DERIVED CONE VIABILITY FACTOR

GRANT INFORMATION

This invention was made with government support under SBIR Grant No. EY016262 awarded by the Department of Health and Human Services of the United States of America, National Institutes of Health. The government may have certain rights in the invention.

BACKGROUND OF THE INVENTION

RdCVF is a thioredoxin-like protein specifically expressed by rod photoreceptor cells in the retina (Léveillard et al. (2004) Nature Genetics 36:755-759 and the supplemental information). Two different RdCVF genes are found in humans and they are designated RdCVF1 and RdCVF2. Both RdCVF genes encode two products via alternative splicing: a full length protein and a C-terminal post-transcriptionally truncated protein, known as RdCVF-long and RdCVF-short, respectively.

RdCVF-short is described as a secreted trophic factor for promoting cone survival, and RdCVF-Long as a redox-active enzyme that interacts with intracellular proteins (Léveillard et al. (2010) Sci Transl Med. 2(26): 26ps16). For example, tau is described as a binding partner for RdCVF-L and tau is exclusively intracellular (Fridlich et al. (2009) Molecular & Cellular Proteomics 8(6):1206-18).

Individuals suffering from some retinal dystrophies were found to have lower levels of RdCVF protein in their eyes than did individuals without retinal dystrophies (PCT Publication WO02/081513).

It has been demonstrated that different forms of RdCVF protein can promote cone photoreceptor cell survival in vitro and in vivo. For example, intraocular injections of the short form of human RdCVF1 (RdCVF1S) protein not only rescued cone cells from degeneration but also preserved their function in animal models of inherited retinal degeneration (Yang et al. (2009) Mol Therapy 17:787-795). However, demonstration of the in vivo cone cell protective effect of this protein required using multiple intraocular injections.

Expression of significant levels of RdCVF at large scale and from gene therapy vectors has been challenging, e.g., see U.S. Patent Publication No. 20110034546, paragraph [0004].

Citation or discussion of a reference herein shall not be construed as an admission that such is prior art to the present invention.

SUMMARY OF THE INVENTION

The present invention relates, in part, to nucleic acids encoding RdCVF, RdCVF expression constructs, RdCVF vectors, methods of expressing RdCVF, methods of slowing, preventing or inhibiting photoreceptor cell (e.g., cone and/or rod cells) death, treating eye diseases, such as retinal dystrophies, and treating neurodegenerative diseases such as Alzheimer's disease, Huntington's disease, Parkinson's disease or an olfactory disease.

The present invention provides compositions, methods for expressing RdCVF proteins from a cell(s) and methods of treatment.

Some embodiments of the invention provide nucleic acids comprising a nucleotide sequence encoding a coding sequence for an RdCVF protein, wherein the RdCVF coding sequence comprises a recoded nucleotide sequence.

The invention also includes viral vectors comprising a nucleic acid, wherein the nucleic acid comprises a nucleotide sequence encoding a coding sequence for an RdCVF protein, wherein the RdCVF coding sequence comprises a recoded nucleotide sequence.

Some embodiments of the invention relate to an isolated cell comprising a nucleic acid of the invention.

Other embodiments of the invention relate to an RdCVF protein produced by a cell of the invention or from a nucleic acid of the invention. In some embodiments, an RdCVF protein is not a naturally occurring RdCVF amino acid sequence.

Included in the invention are also pharmaceutical preparations comprising (i) a pharmaceutically acceptable carrier and (ii) a nucleic acid of the invention, a viral vector of the invention, an RdCVF protein of the invention or a combination thereof.

Methods for producing an RdCVF protein comprising culturing a cell of the invention under conditions that allow for expression and secretion of the RdCVF protein and isolating the RdCVF protein from the cell culture are also provided.

Some embodiments of the invention relate to methods of preserving ocular rod cells comprising administering to the eye of a mammal a nucleic acid of the invention, a viral vector of the invention, an RdCVF protein of the invention or a combination thereof.

The invention also provides methods of treating diseases such as retinal dystrophy, Stargardt's disease, retinitis pigmentosa, dry age-related macular degeneration (dry AMD), geographic atrophy (advanced stage of dry AMD), wet age-related macular degeneration (wet AMD), glaucoma with or without ocular hypertension, diabetic retinopathy, Bardet-Biedel syndrome, Bassen-Kornzweig syndrome, Best disease, choroidema, gyrate atrophy, congenital amaurosis, refsun syndrome, Usher syndrome, thyroid related eye disease, Grave's disease, a disease associated with retinal pigmented epithelial cells, anterior segment disease, lens disease/cataracts, an eye cup disorder, uveitis, Alzheimer's disease, Huntington's disease, Parkinson's disease or an olfactory disease.

Some embodiments of the invention relate to methods of preserving ocular rod cells comprising administering to the eye of a mammal the nucleic acid and/or viral vector of the invention, wherein the nucleic acid and/or the viral vector is administered by subretinal injection and the rod cells are preserved at a site different from the site of the subretinal injection.

Some embodiments of the invention relate to methods of preserving ocular cone cells comprising administering to the eye of a mammal the nucleic acid and/or viral vector of the invention, wherein the nucleic acid and/or the viral vector is administered by subretinal injection and the cone cells are preserved at a site different from the site of the subretinal injection.

The invention also provides methods of secreting an RdCVF protein from a cell comprising administering to the cell a nucleic acid or a viral vector of the invention.

An RdCVF protein can be an RdCVF1 or RdCVF2 protein or a long or short version.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one."

The use of the term/phrase "and/or" when used with a list means one or more of the listed items may be utilized, e.g., it is not limited to one or all of the elements.

This summary of the invention does not necessarily describe all features or necessary features of the invention. The invention may also reside in a sub-combination of the described features.

BRIEF DESCRIPTION OF THE FIGURES

For the purpose of illustrating the invention, there are depicted in the drawings certain embodiments of the invention. However, the invention is not limited to the precise arrangements and instrumentalities of embodiments depicted in the drawings.

FIG. 1 shows an SDS-PAGE analysis of purified recombinant AAV-RdCVF1L and AAV-GFP vector particles. Proteins of a rAAV-GFP preparation (lane 1) and two rAAV-RdCVF1L preparations (lane 2 and 3) were separated by SDS-PAGE and visualized by silver stain analysis.

FIG. 2A shows a Western blot analysis of RdCVF1L expression in rAAV-RdCVF1L vector transduced ARPE-19 cells. Cell lysate of rAAV transduced ARPE-19 cells were separated by SDS-PAGE, and a Western Blot was performed against RdCVF1L protein. Lane 1 shows untransduced ARPE-19 cell lysate, lane 2 and lane 3 show cell lysates of rAAV-GFP and rAAV-RdCVF1L transduced ARPE-19 cell, respectively.

FIG. 2B shows a Western blot analysis of RdCVF1L expression in rAAV-RdCVF1L vector transduced ARPE-19 cells. Supernatant of rAAV transduced ARPE-19 cells were separated by SDS-PAGE, and a Western Blot was performed against RdCVF1L protein. Lane 1 shows supernatant for control, lane 2 and lane 3 show cell supernatant (FIG. 2B) of rAAV-GFP and rAAV-RdCVF1L transduced ARPE-19 cell, respectively.

FIG. 9 shows the annotated nucleotide sequence of rAAV-RdCVF1L.

DETAILED DESCRIPTION

Figure 3:
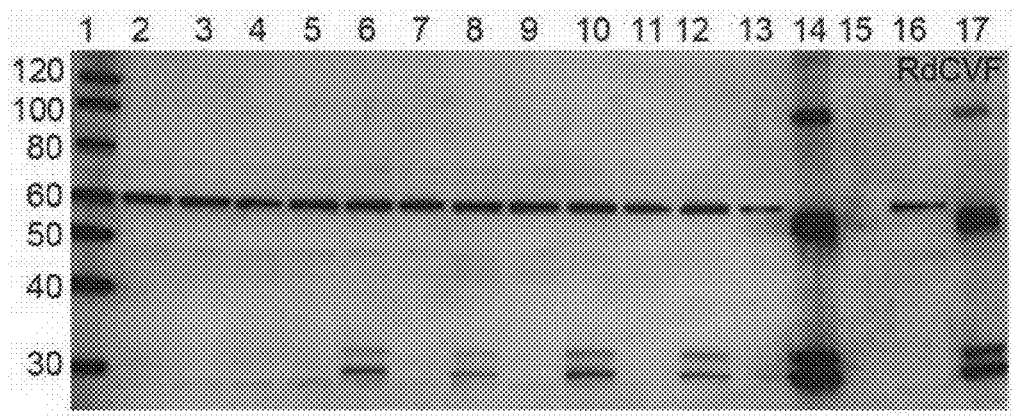
FIG. 3 shows confirmation of increased RdCVF expression in rAAV-RdCVF1L versus rAAV-GFP injected eyes and untreated eyes of normal Balb/C mice by Western blot six weeks after injection of the vectors. Protein extracts from rAAV-RdCVF1L-transduced ARPE-19 cells were used as a positive control (Lane 14 and 17) while untransduced cell extract was used as a negative control (Lane 15). RdCVF protein was detected in rAAV-RdCVF1L injected eyes (Lane 6, 8, 10 and 12) while no or only faint RdCVF-corresponding bands were observed in the untreated contralateral eyes in the same animals (Lane 7, 9, 11 and 13) as well as in rAAV-GFP injected eyes (Lane 2-5). Lane 1 is a protein standard marker. Lane 16 is the protein extract from a wild-type normal mouse eye.

As used herein the transitional term "comprising" is open-ended. A claim utilizing this term can contain elements in addition to those recited in such claim. Thus, for example, the claims can read on methods that also include other steps not specifically recited therein, as long as the recited elements or their equivalent are present.

The terms "identity" and "identical" when used in the context of comparing two sequences, such as nucleotide or amino acid sequences, refers to the percentage of the sequence that aligns between the two sequences. Percent identity can be determined by algorithms commonly employed by those skilled in this art. For example, percent identity can be determined using tools and programs available from the National Center for Biotechnology Information (NCBI) as available on their website. The percent identity of two nucleotide sequences can be determined, for example, using the NCBI/BLAST/blastn suite. Blastn can be used with the parameters set at: expect threshold=10; word size=28; max matches in a query range=0; match/mismatch scores=1, −2; gap costs=existence:5 extension:2.

PCT publications WO2002/081513, WO2008/148860, and WO2009/146183 describe various compositions and methods related to RdCVF. In some cases, RdCVF related compositions and methods described in PCT publications WO2002/081513, WO2008/148860, and WO2009/146183 can be utilized, for example, by replacing an RdCVF encoding nucleic acid, vector or protein with those of the present invention e.g., nucleic acids and vectors comprising a wild-type RdCVF coding sequence).

Some embodiments of the invention provide RdCVF proprotein amino acid sequences such as SEQ ID NOs:2 and 4. The invention also provides nucleotide sequences encoding RdCVF proproteins such as SEQ ID NOs:1, 3 and 11.

The invention also provides methods of treating a disease in a subject where the disease is mediated by or associated with a change in RdCVF1 or RdCVF2 gene expression (e.g., a decrease in the presence of RDCVF1 or RDCVF2 polypeptide in the eye) by the administration of a therapeutically effective amount of a nucleic acid or vector encoding an RDCVF1 or RDCVF2 protein or a related protein or a fragment or portion thereof to a subject.

In another aspect, an RdCVF protein, nucleic acid, vector or composition of the invention can be used in the manufacture of a medicament, e.g., to treat diseases listed herein.

Products, compositions, processes and methods of the invention can be used for, inter alia, research, biological, clinical or therapeutic purposes.

RdCVF

It has been demonstrated that an RdCVF protein can promote cone photoreceptor cell survival in vitro and in vivo. For example, intraocular injections of the short form of human RdCVF1 (RdCVF1S) protein not only rescued cone cells from degeneration but also preserved their function in animal models of inherited retinal degeneration. (Yang et al. (Mol Therapy (2009) 17:787-795 and the supplemental material). RdCVF is expressed by several cell types including rod photoreceptor cells in the retina (Léveillard et al. (2004) Nature Genetics 36:755-759).

Two different RdCVF genes are found in humans and other mammals and they are designated RdCVF1 and RdCVF2. Both RdCVF genes encode two products via alternative splicing: a full length protein and a C-terminal truncated protein, known as RdCVF-long and RdCVF-short, respectively.

In some embodiments, the invention includes a recoded RdCVF coding sequence. A recoded RdCVF coding sequence can encode for any RdCVF protein including any of those disclosed herein. Sequences for various RdCVF proteins can be found in PCT Publication Nos. WO2002081513 and WO2010029130; Chalmel et al. (BMC Molecular Biology (2007) 8:74 pp 1-12 and the supplemental information); Léveillard et al. (Nature Genetics (2004) 36:755-759 and the supplemental information); Yang et al. (Mol Therapy (2009) 17:787-795 and the supplemental material) and GenBank Accession Nos. NP_612463, AAH14127, Q96CM4, EAW84608, CAD67528, Q5VZ03, NP_001155097, NP_660326, CAM24748, CAM14247, AAH22521 and CAD67531. (For clarity, all of these GenBank sequences, as well as all other patent and non-patent publications discussed herein, are incorporated by reference in their entirety.)

In some embodiments, an RdCVF protein is a fragment or an analog of an RdCVF protein that retains a cone cell and/or a rod cell survival activity or protective effect. Methods for measuring these activities or effects are known in the art. For example, Léveillard et al. (Nature Genetics (2004) 36:755-759 and the supplemental information) describes related mouse models and in vitro methods for detecting RdCVF activity. An RdCVF protein or an RdCVF coded for by a nucleic acid, can have an amino acid sequence other than a naturally-occurring amino acid sequence. For example, an RdCVF protein that is not naturally-occurring may contain amino acids in addition to those found in a naturally occurring RdCVF protein (e.g., at the amino or carboxy terminus) and/or may contain single or multiple amino acid substitutions (e.g., conservative or non-conservative amino acid substitutions) as compared to a naturally-occurring RdCVF amino acid sequence. A conservative amino acid substitution generally should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991). Conservative substitutions include, but are not limited to, those from the following groupings: Acidic Residues Asp (D) and Glu (E); Basic Residues Lys (K), Arg (R), and His (H); Hydrophilic Uncharged Residues Ser (S), Thr (T), Asn (N), and Gln (Q); Aliphatic Uncharged Residues Gly (G), Ala (A), Val (V), Leu (L), and Ile (I); Non-polar Uncharged Residues Cys (C), Met (M), and Pro (P); Aromatic Residues Phe (F), Tyr (Y), and Trp (W); Alcohol group-containing residues S and T; Aliphatic residues I, L, V and M; Cycloalkenyl-associated residues F, H, W and Y; Hydrophobic residues A, C, F, G, H, I, L, M, R, T, V, W and Y; Negatively charged residues D and E; Polar residues C, D, E, H, K, N, Q, R, S and T; Positively charged residues H, K and R; Small residues A, C, D, G, N, P, S, T and V; Very small residues A, G and S; Residues involved in turn formation A, C, D, E, G, H, K, N, Q, R, S, P and T; and Flexible residues Q, T, K, S, G, P, D, E and R. In some embodiments of the invention, a non-naturally occurring RdCVF protein has additional amino acids at the amino terminus, e.g., additional amino acids from a heterologous signal peptide. In some embodiments, an RdCVF protein of the invention is initially translated from a nucleotide coding sequence with a signal peptide and in some cases an or part of the amino acids of the signal peptide are retained on an expressed and/or secreted RdCVF protein of the invention.

Recoded RdCVF Coding Sequences

The term "recoded" or "recoded nucleotide sequence" means that at least one native codon is changed to a different codon that encodes for the same amino acid as the native codon. In some embodiments, a recoded RdCVF coding region has at least 2.5%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least or at least 95% of the codons recoded. In some embodiments, about 20-50%, 35-45%, 38-42% or 39-41% or the codons are recoded. In some embodiments, a recoded codon is replaced with a codon that is more prevalently used in humans. In some embodiments, at least 5%, at least 10%, at least 15%, at least 20%, at least 25%, at least 30%, at least 35%, at least 40%, at least 45%, at least 50% or at least 55% of the codons have been replaced with a codon that is more prevalently used in humans In some embodiments, a recoded sequence has between about 70-90%, about 75-85%, about 80-85% or about 82-85% identity with the corresponding native coding sequence. In some embodiments, a recoded nucleotide sequence has at least 15% of the nucleotides different as compared to a corresponding native nucleotide sequence. In some embodiments, a recoded nucleotide sequence is less than 90% identical to a corresponding native nucleotide sequence.

Recoding can also be used to change the chemical make-up of a DNA and/or an RNA coding sequence such as the guanine/cytosine (GC) percentage. In some embodiments, recoding of an RdCVF coding region raises the GC content to at least 60%. In some embodiments, a recoded RdCVF coding region has a GC percentage between 60-64% or 60.4%-63.5%.

Recoding can be used to change the secondary structure of mRNA. Recoding can also be used to remove or add particular motifs or sites to a coding sequence or nucleic acid molecule, such as procarya inhibitory motifs, consensus splice donor sites, cryptic splice donor sites or a combination thereof. In some embodiments, a recoded RdCVF coding sequence has less procarya inhibitory motifs, consensus splice donor sites, cryptic splice donor sites or a combination thereof than the native sequence. In some embodiments, a recoded RdCVF coding sequence contains no procarya inhibitory motifs, no consensus splice donor sites and/or no cryptic splice donor sites.

Hoover et al. (Nucleic Acids Res. (2002) 30:e43, pp 1-7; Fath et al. (PLoS ONE (2011) 6:e17596 pp 1-14); Graf et al. (J Virol (2000) 74:10822-10826; Raab et al. Syst Synth Biol (2010) 4:215-225; and U.S. Patent Application 20070141557 describe recoding coding regions.

In some embodiments of the invention, a recoded RdCVF coding sequence does not contain the initial RdCVF ATG codon and/or RdCVF stop codon (e.g., TAG). For example, an RdCVF recoded coding sequence can be operatively linked 5' or 3' to another coding sequence resulting in a protein comprising a heterologous amino acid sequence, N-terminal and/or C-terminal to the RdCVF amino acid sequence, respectively. In some of these embodiments, the initial RdCVF ATG codon and/or RdCVF stop codon may be deleted or present in the RdCVF coding region. For example, see SEQ ID NO:1 and SEQ ID NO:3. If another coding sequence is fused in frame at the 3'end of an RdCVF coding region, then the native RdCVF stop codon will not typically be present at the end of the RdCVF coding sequence.

In some embodiments, a recoded RdCVF coding region comprises nucleotides 106 to 741 of SEQ ID NO:1, nucleotides 106 to 429 of SEQ ID NO:1, nucleotides 106 to 432 of SEQ ID NO:3 or nucleotides 106 to 744 of SEQ ID NO:3.

In some embodiments, a recoded RdCVF coding sequence is a recoded sequence that codes for amino acids 36-246 of SEQ ID NO:2.

In some embodiments, a coding sequence of the invention codes for a protein containing a signal sequence.

Signal Peptides/Secretion Signals

Signal sequences are translated in frame as a peptide attached, typically, to the amino-terminal end of a polypeptide of choice. A secretory signal sequence will cause the secretion of the polypeptide from the cell by interacting with the machinery of the host cell. As part of the secretory process, this secretory signal sequence will typically be cleaved off or at least partially cleaved off. The term "signal sequence" also refers to a nucleic acid sequence encoding the signal peptide. In some embodiments, a signal sequence is heterologous as compared to a particular RdCVF.

The structure of a typical signal peptide can include three distinct regions: (i) an N-terminal region that contains a number of positively charged amino acids (e.g., lysines and arginines); (ii) a central hydrophobic core region (h-region); (iii) a hydrophilic cleavage region (c-region) that contains the sequence motif recognized by the signal peptidase. (e.g., see von Heijne, G. (1983) Eur. J. Biochem., 133:17-21; von Heijne, G. (1985) J. Mol. Biol., 184:99-105; von Heijne, G. (1997) Protein Engineering (10):1-6). Examples of proteins with signal peptides that can be used in the invention include, but are not limited to, human growth hormone (HGH), bone morphogenetic protein 7 (BMP7), bone morphogenetic protein 2 (BMP2), ciliary neurotrophic factor (CNTF), brain derived neurotrophic factor (BDNF), insulin growth factor 1 (IGF-1), β-glucoronidase (GUSB), glial cell-derived neurotrophic factor (GDNF), hepatocyte growth factor (HGF), vascular endothelial growth factor (VEGF), leukemia inhibitory factor (LIF), immunoglobulin proteins, bovine growth hormone, bovine proalbumin, human proinsulin, human interferon-gamma., human alpha-fibrinogen, human IgG heavy chain, rat amylase, murine alpha-fetoprotein, chicken lysozyme, human placental alkaline phosphatase and Zea mays rein protein 22.1. These signal peptides can be used in accordance with the invention. In some embodiments, a signal peptide used in accordance with the invention is selected from the group consisting of HGH, BDNF, IGF-1 and GUSB. In some embodiments, the signal peptide is from an immunoglobulin such as an IgK.

A signal sequence can be a mammalian, murine or human signal sequence. In some embodiments, a nucleic acid or vector of the invention comprises nucleotides 1-105 of SEQ ID NO:1 or 4-105 of SEQ ID NO:1. In some embodiments, a signal sequence codes for an amino acid sequence comprising amino acids 2-34 of SEQ ID NO:2 or comprises SEQ ID NO:15. A nucleotide sequence coding for a signal peptide can be a wild-type sequence or it can be a recoded sequence.

In some embodiments of the invention, a signal peptide sequence is encoded for the N-terminal or C-terminal of an RdCVF. In some embodiments, the signal peptide directs transit of the protein to secretory pathways, e.g., to the endoplasmic reticulum (ER). In some embodiments, a signal peptide facilitates protein transport from the cytoplasm to destinations outside the cell. Signal peptide sequences may be selected from naturally occurring signal peptide sequences, derivatives thereof, or a synthetic designed sequence. In some embodiments, non-limiting parameters for a designed signal peptide sequences include a sequence of 3-40 residues, comprising a 3- to 20-residue hydrophobic core flanked by several relatively hydrophilic residues.

In some embodiments, a signal peptide sequence lacks a hydrophobic core. Non-limiting examples of mammalian secretory proteins that lack a typical hydrophobic signal sequence that can be used in the invention include, but are not limited to, human IL-1α, IL1β, bFGF, aFGF, PDEGF, anticoagulant protein, lectin L-14, ATL-derived factor, Factor XIIIa, Anchorin CII, lipocortin I, parathymosin, α-prothymosin, and rodent transglutaminase, parathymosin and MDGI.

Nucleic Acids

The invention includes nucleic acids comprising a nucleotide sequence encoding an RdCVF and includes vectors comprising these nucleic acids.

To ensure local and/or long term expression of a nucleic acid of interest, some embodiments of the invention contemplate transducing a cell with a nucleic acid or vector encoding an RdCVF. The instant invention is not to be construed as limited to any one particular nucleic delivery method, and any available nucleic acid delivery vehicle with either an in vivo or in vitro nucleic acid delivery strategy, or the use of manipulated cells (such as the technology of Neurotech, Lincoln, R.I., e.g., see U.S. Pat. Nos. 6,231,879; 6,262,034; 6,264,941; 6,303,136; 6,322,804; 6,436,427; 6,878,544) as well as nucleic acids of the invention encoding an RdCVF per se (e.g., "naked DNA"), can be used in the practice of the invention. Various delivery vehicles, such as vectors, can be used with the invention. For example, viral vectors, amphitrophic lipids, cationic polymers, such as polyethylenimine (PEI) and polylysine, dendrimers, such as combburst molecules and starburst molecules, nonionic lipids, anionic lipids, vesicles, liposomes and other synthetic nucleic acid means of delivery (e.g., see U.S. Pat. Nos. 6,958,325 and 7,098,030; Langer, Science 249:1527-1533 (1990); Treat et al., in "Liposomes" in "The Therapy of Infectious Disease and Cancer"; and Lopez-Berestein & Fidler (eds.), Liss, New York, pp. 317-327 and 353-365 (1989); "naked" nucleic acids and so on can be used in the practice of the instant invention.

In some embodiments, a nucleic acid molecule is used in which the RdCVF coding sequences and any other desired sequences are flanked by regions that promote homologous recombination at a desired site in the genome, thus providing for intrachromosomal expression of the RdCVF nucleic acid (Koller et al., (1989) Proc. Natl. Acad. Sci. USA 86:8932-8935; Zijlstra et al. (1989) Nature 342:435438). Delivery of a nucleic acid into a patient may be either direct, in which case the patient is directly exposed to the nucleic acid or nucleic acid-carrying vector, or indirect, in which case, cells are first transformed with the nucleic acid in vitro, then transplanted into the patient.

A vector is a means by which a nucleic acid of interest (e.g., a therapeutic nucleic acid that can encode a therapeutic protein) is introduced into a target cell of interest. Methods for obtaining or constructing a vector of interest include, but are not limited to, standard gene manipulation techniques, sequencing reactions, restriction enzymes digests, polymerase reactions, PCR, PCR SOEing, ligations, recombinase reactions (e.g., Invitrogen's GATEWAY® technology) other enzymes active on nucleic acids, bacteria and virus propagation materials and methods, chemicals and reagents, site directed mutagenesis protocols and so on, as known in the art, see, for example, the Maniatis et al. text, "Molecular Cloning."

Nucleic acids of the invention will typically comprise a promoter sequence operatively linked to an RdCVF coding sequence. A promoter may be a tissue specific promoter, a cell specific promoter, an inducible promoter, a repressible promoter, a constitutive promoter, a synthetic promoter or a hybrid promoter, for example. Examples of promoters useful in the constructs of the invention include, but are not limited to, a phage lambda (PL) promoter; an SV40 early promoter; a herpes simplex viral (HSV) promoter; a cytomegalovirus (CMV) promoter, such as the human CMV immediate early promoter; a hybrid promoter with CMV enhancer and chicken beta-actin promoter; a tetracycline-controlled transactivator-responsive promoter (tet) system; a long terminal repeat (LTR) promoter, such as a MoMLV LTR, BIV LTR or an HIV LTR; a U3 region promoter of Moloney murine sarcoma virus; a Granzyme A promoter; a regulatory sequence(s) of the metallothionein gene; a CD34 promoter; a CD8 promoter; a thymidine kinase (TK) promoter; a B19 parvovirus promoter; a PGK promoter; a glucocorticoid promoter; a heat shock protein (HSP) promoter, such as HSP65 and HSP70 promoters; an immunoglobulin promoter; an MMTV promoter; a Rous sarcoma virus (RSV) promoter; a lac promoter; a CaMV 35S promoter; and a nopaline synthetase promoter. In some embodiments, a promoter is an MND promoter (Robbins et al., 1997, J. Virol. 71:9466-9474), or an MNC promoter, which is a derivative of the MND promoter in which the LTR enhancers are combined with a minimal CMV promoter (Haberman et al., J. Virol. 74(18):8732-8739, 2000). In some embodiments, an RdCVF coding sequence is operatively linked to a promoter sequence comprising nucleotide sequence 150-812 of SEQ ID NO:11.

In some embodiments, a vector or nucleic acid of the invention comprises an intron, operatively linked to a coding sequence for an RdCVF protein. An intron can be from an RdCVF gene or be a heterologous intron. Heterologous introns are known and non-limiting examples include a human β-globin gene intron and a beta-actin intron. In some embodiments, an intron sequence is a human β-globin gene intron sequence. In some embodiments, an intron sequence comprises nucleotides 820-1312 of SEQ ID NO:11 or 908-1307 of SEQ ID NO:11.

In some embodiments, a nucleic acid of the invention comprises a nucleotide sequence encoding a coding sequence for an RdCVF protein, wherein the RdCVF coding sequence comprises a recoded nucleotide sequence. A nucleic acid can encode for an RdCVF1 protein and/or an RdCVF2 protein. In some embodiments, an RdCVF protein is a short version RdCVF protein. In some embodiments, an RdCVF protein is a long version RdCVF protein. For clarity, an RdCVF protein can be an RdCVF1-short, RdCVF1-long, RdCVF2-short or RdCVF2-long protein. In some embodiments, the RdCVF protein is a human RdCVF protein.

Typically a mammalian nucleotide coding region starts with the nucleotide sequence ATG (initiating methionine codon), such as found in a human RdCVF coding region. As discussed herein, some embodiments of the invention provide a recoded RdCVF coding region and in some further embodiments the coding region is fused, in-frame with a second coding region, e.g., a coding sequence for a signal sequence. In some of these cases, the ATG nucleotide sequence is not necessarily at the start of the RdCVF coding region, e.g., the RdCVF coding region starts by coding for the second amino acid of the particular RdCVF protein. However, the ATG nucleotide sequence can be at the start of the RdCVF coding region, even when the RdCVF coding region is operatively linked to another coding region 5' to the RdCVF coding region.

In some embodiments, a nucleic acid of the invention comprises SEQ ID NOs:1, 3 or 11. In some embodiments, a nucleic acid of the invention comprises nucleotides 150-812, 820-1312 and 1340-2080 of SEQ ID NO:11. In some embodiments, a nucleic acid of the invention comprises nucleotides 150-812, 908-1307 and 1340-2080 of SEQ ID NO:11. In some embodiments, a nucleic acid further comprises nucleotides 2130-2608 of SEQ ID NO:11.

In some embodiments a nucleic acid of the invention comprises a coding region for an RdCVF, wherein the RdCVF coding sequence has been recoded.

In some embodiments of the invention, a nucleic of the invention is in a vector, such as a viral vector.

Viral Vectors

The invention includes viral vectors comprising an RdCVF coding region of the invention. Examples of viral vectors useful in the present invention are described in PCT Publication No. WO08/106644 and U.S. Patent Publication No. US20100120665. In some embodiments, the invention is not limited to a particular viral vector. Viral vectors include, but are not limited to, retroviral vectors, lentiviral vectors, adenoviral vectors (see, for example, U.S. Pat. No. 7,045,344), AAV vectors (e.g., see U.S. Pat. No. 7,105,345), Herpes viral vectors (e.g., see U.S. Pat. Nos. 5,830,727 and 6,040,172), hepatitis (e.g., hepatitis D) viral vectors (e.g., see U.S. Pat. No. 5,225,347), SV40 vectors, EBV vectors (e.g., see U.S. Pat. No. 6,521,449) and Newcastle disease virus vectors (e.g., see U.S. Pat. Nos. 6,146,642, 7,442,379, 7,332,169 and 6,719,979). In some embodiments, a lentiviral vector is an HIV, EIAV, SIV, FIV or BIV vector. In some embodiments, a vector is selected from an AAV vector or an adenoviral vector. The invention also provides a cell that produces a viral vector of the invention.

Vector virions of the invention may be administered in vivo or in vitro to cells (e.g., mammalian cells). Vectors (viral or nonviral) can be used to transduce or transform cells including, but not limited to, undifferentiated cells, differentiated cells, somatic cells, primitive cells and/or stem cells. In some embodiments, stem cells are intended for administration to a human and not for implantation in a suitably pseudopregnant woman for differentiation and development into an infant.

In some embodiments, a viral vector of the invention comprises a decay accelerating factor (DAF). For example, an enveloped viral vector includes a DAF on the viral membrane. In some embodiments, a DAF is a wild-type DAF. In some embodiments, a DAF is part of a fusion protein with an envelope protein, e.g., see Guibinga et al. Mol Ther. 2005 11(4):645-51.

Adenovirus is a non-enveloped, nuclear DNA virus with a genome typically of about 36 kb. The human adenoviruses are divided into numerous serotypes (approximately 47, numbered accordingly and classified into 6 groups: A, B, C, D, E and F).

Recombinant adenoviral vectors have tropism for both dividing and non-dividing cells, minimal pathogenic potential, ability to replicate to high titer for preparation of vector stocks and the potential to carry relatively large nucleotide sequence inserts (Berkner, (1992) Curr. Top. Micro. Immunol. 158:39-66; Jolly, (1994) Cancer Gene Therapy 1:51-64). Adenoviral vectors with deletions of various adenoviral gene sequences have been designed as suitable vehicles for delivery of nucleic acids to cells. In some embodiments, an adenoviral vector of the invention is a helper dependent or a "gutless" adenoviral vector. Adenoviral vectors can be used that are deleted in one or more of the following genes: E1a, E1b, E2a, E2b and E3. Methods for conducting adenovirus-based nucleic acid delivery are described in, e.g., U.S. Pat. Nos. 5,824,544; 5,868,040; 5,871,722; 5,880,102; 5,882,877; 5,885,808; 5,932,210; 5,981,225; 5,994,106; 5,994,132; 5,994,134; and 6,001,557.

AAV vectors are derived from single-stranded (ss) DNA parvoviruses. A single AAV particle can accommodate up to 5 kb of ssDNA, leaving about 4.5 kb for a transgene and regulatory elements. Trans-splicing systems as described, for example, in U.S. Pat. No. 6,544,785, may nearly double this limit and these types of vectors may also be used with the invention. With regard to the invention, essentially AAV of any serotype can be used. In some embodiments of the invention, an AAV1, AAV2, AAV3, AAV4, AAV5, AAV6, AAV7, AAV8 or AAV9 serotype may be used (e.g., see U.S. Pat. Nos. 5,173,414, 5,252,479, 5,552,311, 5,658,776, 5,658,785, 5,763,416, 5,773,289, 5,843,742, 5,869,040, 5,942,496, 5,948,675, 6,001,650 and 7,790,449; PCT Publication No. WO2009134681; Kassim et al., PLoS ONE (2010) 5(10)e13424:1-10; Kotin, Hum Mol Genet (2011) 20(R1):R2-6), although the invention is not limited to these serotypes (see, e.g., Gao et al. (2002) PNAS 99:11854-11859; and Viral Vectors for Gene Therapy: Methods and Protocols, ed. Machida, Humana Press, 2003).

An AAV vector of the invention may also be pseudotyped. Pseudotyped AAV vectors contain the genome of one AAV serotype in the capsid of a second AAV serotype (e.g., see Auricchio et al., (2001) Hum. Mol. Genet., 10(26):3075-81). An AAV vector of the invention may contain a mutated capsid and/or be retargeted. For example, see Grieger et al. (Adv Biochem Eng Biotechnol. (2005) 99:119-45); Goncalves et al. (Mol Ther. (2006) 13(5):976-86); and Warrington et al. (J Virol. (2004) 78(12):6595-609).

In some embodiments of the invention, an AAV vector is coated with polymers, e.g., reactive polymers to reduce natural tropism or natural binding of the AAV vector; to retarget the AAV vector and/or to provide resistance to neutralizing antisera. For example, see Carlisle et al. (J Gene Med. (2008) 10(4):400-11).

Retroviruses are RNA viruses wherein the viral genome is RNA. When a host cell is infected with a retrovirus, the genomic RNA is reverse transcribed into a DNA intermediate which is integrated efficiently into the chromosomal DNA of infected cells. Lentiviruses contain other genes with regulatory or structural function. The use of retroviral vectors for gene delivery is described, for example, in U.S. Pat. No. 6,013,516; and U.S. Pat. No. 5,994,136. Examples of BIV systems are described, for example, in Matukonis et al., 2002 Hum. Gene Ther. 13, 1293-1303; Molina et al., 2002 Virology. 304, 10-23; Molina et al., 2004 Hum. Gene Ther., 15, 65-877; U.S. Pat. Nos. 6,864,085, 7,125,712, 7,153,512; PCT Publication No. WO08/106644 and U.S. Patent Publication No. US20100120665.

A DNA viral vector is a viral vector based on or derived from a virus that has a DNA based genome. A non-enveloped virus viral vector is a viral vector based on or derived from a virus that lacks a lipid-bilayer membrane.

In some embodiments, a viral vector of the invention is an AAV vector. In some embodiments, a viral vector of the invention is not a bovine immunodeficiency viral vector or it is not a lentiviral vector. In some embodiments, a viral vector is selected from the group consisting of a DNA viral vector, a non-enveloped viral vector and an adenoviral vector.

Cellular Delivery of RdCVF, Including Encapsulated Cells

Another approach to gene therapy or protein delivery involves transferring a gene to cells in vitro or ex vivo and then administering the cells to a mammal or patient. Transferring a nucleic acid to cells can be by any method, such as, transfection, microinjection, electroporation, cell fusion, chromosome-mediated gene transfer, microcell-mediated gene transfer, spheroplast fusion, lipofection, microparticle bombardment, calcium phosphate mediated transfection, viral vector or bacteriophage transduction and so on. Optionally, a selectable marker also can be introduced into the cells. If a selectable marker is utilized, the cells can be then placed under selection, e.g., to enhance expression and/or to isolate/select those cells that express the transferred coding region (see, e.g., Loeffler & Behr, Meth. Enzymol. 217:599-618 (1993); Cohen et al., Meth. Enzymol. 217:618-644 (1993); and Cline, Pharmac. Ther. 29:69-92 (1985)). Those cells can then be delivered to a patient directly or after encapsulation.

In some embodiments, a nucleic acid is introduced into a cell prior to in vivo administration of the resulting recombinant cell. In some embodiments, a technique can provide for the stable transfer of the nucleic acid to the cell, so that the nucleic acid is expressible by the cell and in some cases heritable and expressible by its cell progeny. Recombinant cells can be delivered to a patient by various methods. In some embodiments, an RdCVF protein is expressed from a cell via a regulatable, inducible and/or repressible promoter.

In some embodiments, a cell used is autologous, allogeneic or xenogeneic with regard to a patient. In some embodiments, autologous cells are manipulated ex vivo to cause them to contain a nucleic acid of the invention which allows the cell to produce or secrete an RdCVF protein and the cells are introduced back to the patient.

In some embodiments, cells are administered locally (e.g., in a joint, intravitreal, intraretinal, intracranially etc.) or systemically (e.g., i.v.).

In some embodiments, recombinant blood cells (e.g., hematopoietic stem and/or progenitor cells) are administered intravenously. In some embodiments, eye cells and/or pluripotential cells can be injected directly into the eye.

A stem-and/or progenitor cell which can be isolated and maintained in vitro can potentially be used in accordance with some embodiments of the invention. Such stem cells include, but are not limited, to hematopoietic stem cells (HSC), stem cells of epithelial tissues such as the skin and the lining of the gut, embryonic heart muscle cells, liver stem cells (see, e.g., WO 94/08598), and neural stem cells (e.g., Stemple and Anderson (1992) Cell 71:973-985). In some embodiments, the administered cell is a stem cell comprising a nucleic acid of the invention and is capable of expressing and secreting an RdCVF.

Encapsulated cells can allow controlled and/or continuous delivery of a protein, such as RdCVF, in vivo. In some embodiments, cells comprising a nucleic acid of the invention and expressing and/or secreting an RdCVF are encapsulated. In some embodiments, cells are encapsulated within a semipermeable membrane that allows diffusion of RdCVF through the membrane. More information related to encapsulated cells and encapsulated cell implants is found in Sieving et al. (Proc Natl Acad Sci USA, (2006) 103(10): 3896-901); U.S. Pat. Nos. 7,115,257 and 7,820,195; and PCT Publication No. WO2011044216. In some embodiments of the invention, encapsulated cells that express an RdCVF protein are delivered to an animal.

In some embodiments, encapsulated cells are implanted into a mammal, e.g., implanted in the eye, brain or olfactory region. In some embodiments, encapsulated cells are retinal pigment epithelial cells, e.g., ARPE-19 (available from ATCC, Manassas, Va.). In some embodiments, encapsulated cells are used to deliver RdCVF to the eye, e.g., to the back of the eye.

In some embodiments, an encapsulated cell implant of the invention is comprised of cells that are encapsulated in a section of semi-permeable hollow fiber membrane and the cells have been genetically modified to produce an RdCVF. In some embodiments, an encapsulated cell implant has a suture loop at one end to anchor it to the sclera in the vitreo-retinal body inside the eye. In some embodiments, an encapsulated cell implant is 3, 4, 5, 6, 7, 8, 9 or 10 mm in length.

RdCVF Protein Secretion and Production

Nucleic acids and viral vectors of the invention can be used to express, produce and/or secrete an RdCVF from a cell. This expression, production and/or secretion can occur in vitro, in vivo or ex vivo.

Some embodiments of the invention provide methods of secreting an RdCVF protein from a cell comprising administering to the cell a nucleic acid and/or a viral vector of the invention. In some embodiments, the cell can be a mammalian cell, a human cell, an ocular cell, a retinal pigment epithelial (RPE) cell, a rod cell or a cone cell.

Some embodiments of the invention utilize vertebrate or mammalian cells. Examples of useful mammalian host cell lines are a monkey kidney CVI cell line transformed by SV40 (e.g., COS-7, ATCC CRL 1651); human embryonic kidney line (e.g., 293 or 293T cells including either cell line subcloned for growth in suspension culture, Graham et al., J. Gen Virol. 36:59 (1977) such as 293 Freestyle (Invitrogen, Carlsbad, Calif.)) or 293FT; baby hamster kidney cells (e.g., BHK, ATCC CCL 10); Chinese hamster ovary cells (CHO cells); Chinese hamster ovary cells/-DHFR (e.g., CHO, Urlaub et al., Proc. Natl. Acad. Sci. USA 77:4216 (1980)); mouse sertoli cells (e.g., TM4, Mather, Biol. Reprod. 23:243-251 (1980)); monkey kidney cells (e.g., CVI ATCC CCL 70); African green monkey kidney cells (e.g., VERO-76, ATCC CRL-1587); human cervical carcinoma cells (e.g., HELA, ATCC CCL 2); canine kidney cells (e.g., MOCK, ATCC CCL 34); CF2TH cells; buffalo rat liver cells (e.g., BRL 3A, ATCC CRL 1442); human lung cells (e.g., W138, ATCC CCL 75); human liver cells (e.g., Hep G2, HB 8065); mouse mammary tumor cells (e.g., MMT 060562, ATCC CCL51); TRI cells (Mather et al., Annals N.Y. Acad. Sci. 383:44-68 (1983)); MRC 5 cells; ARPE-19 cells (ATCC) and FS4 cells.

In some embodiments, a cell is selected from the group consisting of a 293 cell, a CHO cell, a PerC6 cell, a Vero cell, a BHK cell, a HeLa cell, a COS cell, a MDCK cell, a 3T3 cell or a WI38.

Some embodiments of the invention provide an isolated cell comprising a nucleic acid of the invention. In some embodiments, the nucleic acid is integrated into the cellular genome/DNA.

The invention also includes methods for producing an RdCVF protein comprising culturing a cell under conditions that allow for expression and secretion of the RdCVF protein and isolating the RdCVF protein from the cell culture, wherein the cell comprises a nucleic acid of the invention that codes for and allows the expression of the RdCVF protein, e.g., secretion of an RdCVF protein. In some embodiments, the nucleic acid comprises a nucleotide sequence comprises a coding sequence for an RdCVF protein, wherein the RdCVF coding sequence comprises a recoded sequence. The RdCVF protein can be an RdCVF 1 or 2 protein or be the long or short form. In some embodiments, these methods further comprise purification of the RdCVF protein from the cell and/or culture supernatant.

The invention also includes an RdCVF protein expressed by a cell from a nucleic acid of the invention. The invention also provides secreted forms of RdCVF proteins of the invention and compositions comprising a secreted RdCVF protein of the invention.

In some embodiments, an RdCVF protein expressed from a cell is purified to at least 90%, at least 93%, at least 95%, at least 98%, at least 99.5% or at least 99.9% pure in relation to total protein.

Compositions, Formulations and Preparations

Some embodiments of the invention provide compositions, formulations or preparations, e.g., pharmaceutical compositions, containing a nucleic acid of the invention, a vector of the invention, a RdCVF protein of the invention, or any combination thereof.

Formulations (e.g., for injection) are generally, but not necessarily, biocompatible solutions of the active ingredient, e.g., comprising Hank's solution, Ringer's solution or phosphate buffered saline. In some embodiments, a formulation or pharmaceutical composition comprises one or more of the following: citrate, NaCl, potassium chloride (KCl), calcium chloride dihydrate ($CaCl_2.2H_2O$), magnesium chloride hexahydrate ($MgCl_2.6H_2O$), sodium acetate trihydrate ($CH_3CO_2Na.3H_2O$), sodium citrate dihydrate ($C_6H_5O_7Na_3.2H_2O$), sucrose, sodium hydroxide and/or hydrochloric acid (to adjust pH) and water. The preceding list includes some molecules that are listed as particular hydrates, e.g., dihydrate, trihydrate, hexahydrate, etc. It is understood that various hydrates of these compounds can be used in the invention and the invention is not limited to these particular hydrate forms of the listed molecules. In some embodiments, a formulation or pharmaceutical composition comprises one or more ingredients selected from the group consisting of histidine, $MgCl_2$, trehalose, a polysorbate, polysorbate 20, NaCl, sucrose, arginine and proline. In some embodiments, a formulation comprises one or more of the following: histidine; α,α-trehalose dehydrate; $MgCl_2$; a polysorbate such as polysorbate 20; and NaCl. In some embodiments, a formulation or pharmaceutical composition comprises one or more of the following: phosphate buffered saline (PBS) and pluronic F-68. In some embodiments, pluronic F-68 concentration can be 0.0001%, 0.001%, 0.005%, 0.01% or 0.1%.

Examples of suitable formulations and formulatory methods for a desired mode of administration may be found in Remington's Pharmaceutical Sciences, latest edition, Mack Publishing Co., Easton, Pa. and in U.S. Pat. No. 7,208,577.

In some embodiments, a composition for use in vivo contains a "carrier" or a "pharmaceutically acceptable carrier". The term "carrier" refers to a diluent, adjuvant, excipient, or vehicle with which the a nucleic acid, vector or protein of the invention is administered. The term "carrier' includes, but is not limited to, either solid or liquid material, which may be inorganic or organic and of synthetic or natural origin, with which an active component(s) of the composition is mixed or formulated to facilitate administration to a subject. Any other materials customarily employed in formulating a pharmaceutical are suitable. Pharmaceutical carriers can differ from typical solutions and suspensions in that they are specifically prepared for use in vivo to exclude substances that may be harmful to the host to whom the composition is administered (e.g., removal of bacterial toxins).

Examples of suitable liquid carriers include water and aqueous solutions containing oxygenated organic compounds such as ethanol. Buffers and other materials normally present in pharmaceutical preparations, such as flavoring and suspending agents, can also be present. In general, a suitable oil(s), saline, aqueous dextrose (glucose), and related sugar solutions and glycols such as propylene glycol or polyethylene glycols are typically suitable carriers for parenteral solutions. In some embodiments, solutions for parenteral administration contain a water soluble salt of the active ingredient, suitable stabilizing agents, and if desirable or necessary, buffer substances. Antioxidizing agents such as sodium bisulfite, sodium sulfite, or ascorbic acid, either alone or combined, can be used as stabilizing agents. Also used are citric acid and its salts and sodium EDTA. In addition, parenteral solutions can contain preservatives, such as benzalkonium chloride, methyl- or propyl-paraben and chlorobutanol.

Carriers can include carbohydrates such as trehalose, mannitol, glutathione, xylitol, sucrose, lactose and sorbitol. Other ingredients for use in formulations may include, for example, DPPC (1,2-Didecanoyl-sn-glycero-3-phosphocholine), DOPE (1,2-Dioleoyl-sn-glycero-3-phosphoethanolamine), DSPC (1,2-Distearoyl-sn-glycero-3-phosphocholinez 1,2-Distearoyl-sn-glycero-3-phosphocholine) and DOPC (1,2-Dioleoyl-sn-glycero-3-phosphocholine). Natural or synthetic surfactants may be used. Polyethylene glycol may be used (even apart from its use in derivatizing a protein). Dextrans, such as cyclodextran, may be used. In some embodiments, cyclodextrin, tertiary amines and/or beta-cyclodextrin may be used. Bile salts and other related enhancers may be used. Cellulose and cellulose derivatives may be used. Amino acids may be used, such as use in a buffer formulation. Also, the use of liposomes, microcapsules or microspheres, inclusion complexes, or other types of carriers is contemplated.

A composition, if desired, can also contain wetting and/or emulsifying agents, and/or pH buffering agents. Where necessary, a composition may also include a solubilizing agent and/or a local anesthetic such as lignocaine to ease pain at the site of the injection.

In some embodiments, a pharmaceutical preparation or composition of the invention comprises a (i) pharmaceutically acceptable carrier and (ii) a nucleic acid of the invention, a viral vector of the invention, an RdCVF protein of the invention or any combination thereof.

Administration, Delivery and Treatment

It is understood that when introduction or administration of a nucleic acid or vector encoding an RdCVF protein is discussed, that the invention also contemplates the introduction or administration of the RdCVF protein itself. It is understood that when introduction of an RdCVF protein is discussed, that the invention also contemplates the introduction of a nucleic acid or vector encoding an RdCVF protein.

In some embodiments, compositions of the invention can be administered locally or systemically. Useful routes of administration are described herein and known in the art. Methods of introduction or administration include, but are not limited to, intradermal, intramuscular, intraperitoneal, intravenous, subcutaneous, intranasal, intratracheal, topical, inhaled, transdermal, rectal, parenteral routes, epidural, intracranial, into the brain, intraventricular, subdural, intraarticular, intrathecal, intracardiac, intracoronary, intravitreal, subretinal, intraanterior chamber of the eye, locally on the cornea, subconjunctival, subtenon injection, by applying eyedrops, oral routes, via balloon catheter, via stent or any combinations thereof. Systemic administration may be, but is not limited to, by intravenous or intra-arterial injection or by transmucosal, subcutaneous, transdermal and/or intraperitoneal delivery.

In some embodiments, e.g., comprising administration to the eye, an RdCVF encoding vector or nucleic acid of the invention is administered about once every week, month, 2 months, 3 months, 6 months, 9 months, year, 18 months, 2 years, 30 months, 3 years, 5 years, 10 years or as needed. In some embodiments, e.g., comprising administration to the eye, an RdCVF encoding vector or nucleic acid of the invention is administered from about every 1 to 4 weeks, about every 4 to 8 weeks, about every 1 to 4 months, about every 3 to 6 months, about every 4 to 8 months, about every 6 to 12 months, about every 9 to 15 months, about every 12 to 18 months, about every 15 to 21 months, about every 18 to 24 months, about every 1 to 2 years, about every 1.5 to 3 years, about every 2 to 4 years, about every 3 to 5 years, about every 5 to 7 years, about every 7 to 10 years or about every 10 to 20 years. It is expected that administration of a vector coding for an RdCVF protein would be less frequent than administration of the RdCVF protein itself. In some embodiments of the invention, a pharmaceutical preparation comprises a vector encoding an RdCVF protein of the invention and the pharmaceutical preparation is administered only once to the patient.

In some embodiments, an RdCVF protein of the invention is administered by intravitreal or subretinal injection to a human eye. In some embodiments, about 15 μg to about 5 mg; about 15 μg to about 500 μg; about 100 μg to about 900 μg; about 300 μg to about 700 μg; about 500 μg to about 1 mg; about 1 mg to about 5 mg; about 1 mg; or about 500 μg of an RdCVF protein is administered by intravitreal or subretinal injection to a human eye.

In some embodiments, an RdCVF protein is administered by subretinal injection or intravitreal injection of an AAV vector that encodes RdCVF. In some embodiments, about $5 \times 10^8$ to about $1 \times 10^9$; about $5 \times 10^8$ to about $7.5 \times 10^8$; about $7.5 \times 10^8$ to about $1 \times 10^9$; about $6 \times 10^8$ to about $9 \times 10^8$; about $7 \times 10^8$ to about $8 \times 10^8$; about $5 \times 10^8$; about $6 \times 10^8$; about $7 \times 10^8$; about $8 \times 10^8$; about $9 \times 10^8$; or about $1 \times 10^9$ vector genome copy (GC) number of an AAV vector is administered by subretinal injection. In some embodiments, about $5 \times 10^8$ to about $1 \times 10^{10}$; about $5 \times 10^8$ to about $5 \times 10^9$; about $5 \times 10^8$ to about $2 \times 10^9$; about $2 \times 10^9$ to about $5 \times 10^9$; about $5 \times 10^9$ to about $1 \times 10^{10}$; about $5 \times 10^8$ to about $1 \times 10^9$; about $1 \times 10^9$ to about $3 \times 10^9$; about $3 \times 10^9$ to about $6 \times 10^9$; about $6 \times 10^9$ to about $1 \times 10^{10}$; about $1 \times 10^9$ to about $1 \times 10^{10}$; about $1 \times 10^{10}$ to about $1 \times 10^{11}$; or $1 \times 10^{11}$ to about $1 \times 10^{12}$ GC of an AAV vector is administered by intravitreal injection. It is understood that the amount of AAV vector is sometimes measured in transducing units or in GC number. GC numbers are typically between 25-300 times higher than when the same AAV vector sample is measured for transducing units.

In some embodiments, an anti-inflammatory may be delivered in combination with an RdCVF protein, vector or nucleic acid of the invention. An anti-inflammatory may be delivered prior to, concurrently with, and/or after administration of a molecule or vector of the invention. In some embodiments, an anti-inflammatory is administered in the same solution and/or same syringe as an RdCVF protein, nucleic acid or vector of the invention. In some embodiments, an RdCVF protein, nucleic acid or vector of the invention and an anti-inflammatory are co-administered to the eye.

Many anti-inflammatory drugs are known in the art and include, but are not limited to, dexamethasone, dexamethasone sodium metasulfobenzoate, dexamethasone sodium phosphate, fluorometholone, bromfenac, pranoprofen, cyclosporine ophthalmic emulsion (e.g., RESTASIS™), naproxen, glucocorticoids, ketorolac, ibuprofen, tolmetin, non-steroidal anti-inflammatory drugs, steroidal anti-inflammatory drugs, diclofenac, flurbiprofen, indomethacin, and suprofen.

Some embodiments of the invention include administration of both an RdCVF protein and a vector encoding it. An RdCVF protein may be delivered prior to, concurrently with, and/or after administration of a vector of the invention. In some embodiments, an RdCVF protein is administered in the same solution and/or same syringe as a vector of the invention. In some embodiments, a vector of the invention and an RdCVF protein are co-administered to the eye.

In some embodiments of the invention, a gene delivery system can result in transduction and/or stable integration of a gene or coding region for an RdCVF protein into a target cell. In some embodiments, target cells are mammalian cells such as primate cells or human cells. In some embodiments, target cells are cells of the eye, such as retinal pigment epithelial cells, rod photoreceptor cells, cone photoreceptor cells, bipolar cells, horizontal cells, amacrine cells, ganglion cells, retinal cells, or pluripotential cells. Target cells can be in vitro, ex vivo or in vivo. In some embodiments, a target cell is a stem cell. Stem cells include, but are not limited to, pluripotent stem cells, totipotent stem cells, hematopoietic stem cells, cancer stem cells and embryonic stem cells. In some embodiments, pluripotential cells contemplated herein are not those for propagating a living entity from a zygote or blastomere. The instant invention also contemplates the use of a partially undifferentiated cell for implantation into the eye of a patient in need of treatment, e.g., to regenerate cells of the eye.

The invention also provides methods of treatment. In some embodiments, the invention provides methods of preserving ocular rod cells comprising administering to the eye of a mammal a nucleic acid of the invention, a viral vector of the invention, an RdCVF protein of the invention, a pharmaceutical composition of the invention or a combination thereof. In some embodiments, a viral vector and/or nucleic acid of the invention is administered by subretinal injection, intravitreal injection, injection to the intraanterior chamber of the eye, subconjunctival injection, subtenon injection or any combination thereof. In some embodiments, a human is treated. In some embodiments, the mammal to be treated suffers from an ocular disease selected from the group consisting of a retinal dystrophy, Stargardt's disease, retinitis pigmentosa, dry age-related macular degeneration (dry AMD), geographic atrophy (advanced stage of dry AMD), wet age-related macular degeneration (wet AMD), glaucoma/ocular hypertension, diabetic retinopathy, Bardet-Biedel syndrome, Bassen-Kornzweig syndrome, Best disease, choroidema, gyrate atrophy, congenital amaurosis, refsun syndrome, Usher syndrome, thyroid related eye disease, Grave's disease, a disease associated with retinal pigmented epithelial cells, anterior segment disease, lens disease/cataracts, an eye cup disorder, or uveitis. In some embodiments, the preserved ocular rod cell does not contain a nucleic acid and/or viral vector of the invention. For example, the preserved ocular cell is not preserved through transduction of the preserved ocular cell itself.

Some embodiments of the invention, provide a method of preserving ocular rod cells comprising administering to the eye of a mammal a nucleic acid and/or viral vector of the invention, wherein the nucleic acid and/or the viral vector is administered by subretinal injection and the rod cells and/or cones cells are preserved at a site at least 1 mm, at least 2 mm, at least 3 mm, at least 5 mm, at least 7 mm, at least 10 mm, at least 15 mm, at least 20 mm or at least 25 mm from the site of the subretinal injection. For example and not wishing to be bound by theory, the cells transduced with the nucleic acid or viral vector at the subretinal injection site expresses and/or secrete an RdCVF-long and/or an RdCVF-short protein which can provide an ocular rod and/or cone preserving effect at a site distant to the transduced cell or injection site.

In addition to its expression in the eye, RdCVF protein is also naturally expressed in other tissues. Using a proteomics approach 90 proteins were found to interact with RdCVFL including the microtubule-binding protein tau (Fridlich et al. Mol Cell Proteomics (2009) 8(6):1206-1218). Fridlich et al. demonstrated that the level of phosphorylation of TAU is increased in the retina of the Nxnl1$^{-/-}$ (RdCVF1-/-) mice as it is hyperphosphorylated in the brain of patients suffering from Alzheimer disease, presumably in some cases through oxidative stress. Fridlich et al. also showed that RdCVFL inhibits TAU phosphorylation. Cronin et al. (Cell Death and Differentiation (2010) 17:1199-1210) found that Nxnl1-/- (RdCVF1-/-) retinas contained aggregated TAU protein, as found in the brain of patients suffering from Alzheimer's disease.

Mice lacking RdCVF2 have impaired vision and olfaction. Normal mice express RdCVF2 in the olfactory epithelium. Jaillard et al. (ARVO meeting (2009) program#/ poster# 491/D636) reported that olfactory neurons were found to survive to a higher rate when cultured in the presence of RdCVF2. Jaillard et al. also compared RdCVF2-/- to control mice, by performing olfactory discrimination learning tests. By 12 months of age, the RdCVF2-/- mice failed to respond correctly to the stimulus.

RdCVF proteins have neuroprotective activity and are not only a factor for cone and/or rod survival, but are general neuron survival factors.

Therefore based on the above, an RdCVF encoding nucleic acid, viral vector or RdCVF protein of the invention can be used to treat or ameliorate Alzheimer's disease, Huntington's disease, Parkinson's disease and olfactory diseases.

The invention includes methods of treating a disease comprising administering to a mammal a nucleic acid of the invention, a viral vector of the invention, an RdCVF protein of the invention, a pharmaceutical composition of the invention or a combination thereof, wherein the disease is selected from the group consisting of Alzheimer's disease, Huntington's disease, Parkinson's disease and an olfactory disease. In some embodiments, the viral vector of this invention is an AAV vector.

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Whereas, particular embodiments of the invention have been described herein for purposes of description, it will be appreciated by those skilled in the art that numerous variations of the details may be made without departing from the invention as described in the appended claims.

All publications, patents and patent applications mentioned in this specification are herein incorporated by reference in their entirety into the specification to the same extent as if each individual publication, patent or patent application was specifically and individually indicated to be incorporated herein by reference. Also incorporated by reference is any supplemental information that was published along with any of the aforementioned publications, patents and patent applications. For example, some journal articles are published with supplemental information that is typically available online Example 1

Recoded Coding Sequences for RdCVF1 Long and Short Forms

Recoded human RdCVF1S and RdCVF1L nucleotide coding regions were designed (e.g., nucleotides 106-741 of SEQ ID NO:1, nucleotides 106-744 of SEQ ID NO:3, SEQ ID NO:12 or 14). GENEART® (Regensburg, Germany) synthesized nucleic acid sequences that, among other things, contained codon optimized nucleotide coding sequences for RdCVF1S and RdCVF1L. These coding sequences were also recoded to minimize motifs such as procarya inhibitory motifs, consensus splice donor sites and cryptic splice donor sites.

The recoding of a human RdCVF1L coding sequence also provided a recoded RdCVF1S coding region, nucleotides 1-327 of SEQ ID NO:12 with a stop codon at the 3' end.

```
Alignment of a native RdCVF1L coding region to a recoded coding region
RdCVF1L (1-639): Identities = 529/639 (82.8%) 89/213 codons different (41.7%)
RdCVF1S (1-327): Identities = 274/327 (83.8%) 44/109 codons different (40.4%)
RdCVF1S (1-327 & TGA) Identities = 277/330 (83.9%) 44/110 codons different (40.0%)
ATGGCCTCCCTGTTCTCTGGCCGCATCCTGATCCGCAACAATAGCGACCAGGACGAGCTG    60
||||||  |||||||   |  ||| ||||||||| | |||||| |||||||||||||||||
ATGGCCAGCCTGTTCAGCGGCCGGATCCTGATCAGGAACAACAGCGACCAGGACGAGCTG    60

GATACGGAGGCTGAGGTCAGTCGCAGGCTGGAGAACCGGCTGGTGCTGCTGTTCTTTGGT   120
|| || |||||| || |    | ||||||||||||||| | |||||||||||||||||||
GACACCGAGGCCGAAGTGAGCAGGAGGCTGGAGAACAGACTGGTGCTGCTGTTCTTTGGC   120

GCTGGGGCTTGTCCACAGTGCCAGGCCTTCGTGCCCATCCTCAAGGACTTCTTCGTGCGG   180
|| || || || ||  |||| |||||||||||||||||||| |||| ||||| ||| ||
GCCGGAGCCTGCCCTCAGTGCCAGGCCTTCGTGCCCATCCTGAAGGATTTCTTTGTGAGG   180
```

```
                                                                    -continued
CTCACAGATGAGTTCTATGTACTGCGGGCGGCTCAGCTGGCCCTGGTGTACGTGTCCCAG        240
|| || || ||||||||  |||  || ||  || ||||||||||||||||  |||  ||||
CTGACCGACGAGTTCTACGTGCTGAGAGCCGCCCAGCTGGCCCTGGTGTATGTGAGCCAG        240

GACTCCACGGAGGAGCAGCAGGACCTGTTCCTCAAGGACATGCCAAAGAAATGGCTTTTC        300
|||   |||  ||||||||||||||||||| ||||||||||||||||||  |||||  |||
GACAGCACCGAGGAGCAGCAGGACCTGTTCCTGAAGGACATGCCCAAGAAGTGGCTGTTC        300 short ← →long
CTGCCCTTTGAGGATGATCTGAGGAGG↓GACCTCGGGCGCCAGTTCTCAGTGGAGCGCCTG       360
||||||||| ||||| || | ||| || |||||  | ||||||   |||||| | |||
CTGCCCTTCGAGGACGACCTGAGAAGA↑GACCTGGGCAGGCAGTTCAGCGTGGAGAGACTG       360

CCGGCGGTCGTGGTGCTCAAGCCGGACGGGGACGTGCTCACTCGCGACGGCGCCGACGAG       420
|| || ||  ||||||||| || ||| || || |||||||| ||   ||| ||||||||||
CCCGCCGTGGTGGTGCTGAAGCCTGATGGCGACGTGCTGACCAGAGATGGCGCCGACGAG       420

ATCCAGCGCCTGGGCACCGCCTGCTTCGCCAACTGGCAGGAGGCGGCCGAGGTGCTGGAC       480
||||||  | ||||||||||||||||||||||||||||||||||  |||||||||  |||||
ATCCAGAGACTGGGCACCGCCTGCTTCGCCAACTGGCAGGAGGCCGCCGAGGTCCTGGAC       480

CGCAACTTCCAGCTGCCAGAGGACCTGGAGGACCAGGAGCCACGGAGCCTCACCGAGTGC       540
 | ||||||||||||||||| | ||| ||||||||| ||||||| |   ||| ||||||||||
AGAAACTTCCAGCTGCCCGAGGATCTGGAGGATCAGGAGCCCAGATCCCTGACCGAGTGC       540

CTGCGCCGCCACAAGTACCGCGTGGAAAAGGCGGCGCGAGGCGGGCGCGACCCCGGGGGA       600
||| | ||||||||||||||  |||||| ||  ||||| | || |  |||||  || ||
CTGAGGCGGCACAAGTACAGAGTGGAGAAGGCCGCCAGAGGCGGCAGAGACCCTGGCGGC       600

GGGGGTGGGGAGGAGGGCGGGGCCGGGGGGCTGTTCTGA                             639    (SEQ ID NO: 7)
|| || || ||||||||||  |||||  || |||||||||
GGAGGAGGAGAGGAGGGCGGAGCCGGCGGACTGTTCTGA                             639    (SEQ ID NO: 12)
```

Recoding of a native RdCVF1L coding sequence to SEQ ID NO:12 removed 2 procarya inhibitory motifs, 1 consensus splice donor site and 3 cryptic splice donor sites leaving none of these elements in the recoded sequence (SEQ ID NO:12). Recoding also changed the average GC content from 65% to 63%.

Nucleotides 1-327 of SEQ ID NO:12 also provide a recoded coding sequence for RdCVF1S but without a stop codon, such as TGA.

```
Alignment of a native RdCVF1S coding region to a recoded coding region
Identities = 278/330 (84.2%) 43/110 codons different (39.1%)
ATGGCCTCCCTGTTCTCTGGCCGCATCCTGATCCGCAACAATAGCGACCAGGACGAGCTG        60
||||||  ||||||| |||||  | |||||||||| |||||||  |||||||||||||||||
ATGGCCAGCCTGTTCAGCGGCCGGATCCTGATCAGGAACAACAGCGACCAGGACGAGCTG        60

GATACGGAGGCTGAGGTCAGTCGCAGGCTGGAGAACCGGCTGGTGCTGCTGTTCTTTGGT       120
|| || ||||| || || |    ||||||||||||||| ||||||||||||||||||||
GACACCGAGGCCGAAGTGAGCAGGAGGCTGGAGAACAGACTGGTGCTGCTGTTCTTTGGC       120

GCTGGGGCTTGTCCACAGTGCCAGGCCTTCGTGCCCATCCTCAAGGACTTCTTCGTGCGG       180
|| || ||  || || |||||||||||||||||||||||||| ||||| ||||| ||||||
GCCGGAGCCTGCCCTCAGTGCCAGGCCTTCGTGCCCATCCTGAAGGATTTCTTTGTGCGG       180

CTCACAGATGAGTTCTATGTACTGCGGGCGGCTCAGCTGGCCCTGGTGTACGTGTCCCAG       240
|| || || ||||||||   |||  || ||  || ||||||||||||||||  |||  ||||
CTGACCGACGAGTTCTACGTGCTGAGAGCCGCCCAGCTGGCCCTGGTGTATGTGAGCCAG       240

GACTCCACGGAGGAGCAGCAGGACCTGTTCCTCAAGGACATGCCAAAGAAATGGCTTTTC       300
|||   |||  ||||||||||||||||||| ||||||||||||||  |||||  |||||||
GACAGCACCGAGGAGCAGCAGGACCTGTTCCTGAAGGACATGCCCAAGAAGTGGCTGTTC       300

CTGCCCTTTGAGGATGATCTGAGGAGGTGA                                      330    (SEQ ID NO: 13)
||||||||| ||||| || ||| |  | |||
CTGCCCTTCGAGGACGACCTGCGGAGATGA                                      330    (SEQ ID NO: 14)
```

Recoding of a native RdCVF1S coding sequence to SEQ ID NO:14 removed 1 procarya inhibitory motif, 1 consensus splice donor site and 2 cryptic splice donor sites leaving none of these elements in the recoded sequence (SEQ ID NO:14). Recoding also changed the average GC content from 58% to 61%.

Example 2

In vitro Expression of Long Form Rod-Derived Cone Viability Factor Mediated by Adeno-Associated Viral Vector Plasmid Cloning The cDNA of the short form of the RdCVF protein was amplified by PCR from the nucleic acid synthesized by GENEART® and cloned into pSecTag2A plasmid (Invitrogen, Catalog No. V900-20) that incorporated a mouse Igk signal peptide sequence such that the Igk signal peptide DNA sequence is oriented five prime to an RdCVFS coding sequence. The resulting plasmid was designated pAVTrRd034. The size and orientation of pAVTrRd034 was confirmed using restriction enzyme digests. The Igk-RdCVFS sequence was amplified by PCR from pAVTrRd034 and inserted into the adeno-associated virus vector plasmid pAAV-MCS (Cell Biolabs, San Diego, Calif.), creating the plasmid pAAV-SRd269 (SEQ ID NO:8). The codon-optimized long form of RdCVF was amplified by PCR and inserted into the in-house cloning plasmid pAVT001, creating the plasmid pAVTLrRd055 (SEQ ID NO:9). Plasmids pAVTLrRd055 and pAAV-SRd269 were double digested with Bgl II and Stu I. The 4.8 kb band from pAAV-SRd269 and the 540 by band from pAVTLrRd055 were ligated, creating pAAV-LRd268 (SEQ ID NO:10) that contained a recoded coding sequence for long RdCVF. The size and orientation of pAAV-LRd268 was confirmed using restriction enzyme digests.

Because the N-terminal sequences of the short and the long form of the RdCVF protein is identical, the end of the short RdCVF DNA sequence of pAVTrRd034 was exchanged for the end of the codon-optimized long RdCVF DNA sequence from the plasmid pAVTLrRdCVF055, thereby generating the rAAV plasmid pAAV-LRd268, containing the following features in between the AAV-ITRs:

CMV promoter—β-globin intron—Igk-RdCVF1L—Poly A

Production and Purification of Recombinant AAV-RdCVF1L and AAV-GFP Vectors

Plasmids pAAV-LRd268, pHELPER (Cell BioLabs, Catalog No. 340202), and pRC2 (Cell BioLabs, Catalog No. 340201) were transformed into DH10B competent bacteria cells (Invitrogen, Catalog No. 18297-010) and scaled up using the Qiagen EndoFree Plasmid Maxi Kit or EndoFree Plasmid Mega Kit according to the manufacturer's instructions. The plasmid concentrations were determined using a Beckman DU-600 spectrophotometer. Each plasmids identity was confirmed by restriction digests and analysis.

To produce rAAV-RdCVF1L vector, 293AAV cells (Cell BioLabs, Catalog No. AAV-100) were seeded at 4 million cells per 15 cm dish in cDMEM (DMEM supplemented with 10% FBS, 1% Glutamine, 1% non-essential amino acids, and 1% Penicillin/Streptomycin). The following day the medium was replaced with 25 mL fresh cDMEM. Two hours later the transfection was performed. Water (57.4 mL) was mixed with 1.3 mg pHELPER, 650 µg pRC2, 650 µg pAAV-LRd268, and 8.1 mL 2 M $CaCl_2$ (water/plasmid/$CaCl_2$ mix). A 12.5 mL volume of 2×HBS (Lonza, Sku: RR07005) was transferred into each of five 50 mL conical tubes. While vortexing, 12.5 mL of the water/plasmid/$CaCl_2$ mix was slowly added to each of the conical tubes containing 2×HBS. After a 5-minute incubation, 2.5 mL of the suspension was added to each cell culture dish containing the 293AAV cells.

The following day the medium was replaced with 25 mL new cDMEM medium per dish. Two days later the cells were harvested using a cell lifter and the cell/medium mix was transferred into 250 mL conical tubes. The samples were centrifuged at 3,000 rpm for 15 minutes at 4° C., the supernatant was discarded and the cell pellets resuspended in 110 mL DMEM. The resuspended cell samples were aliquoted (30 mL) into 50 mL conical tubes and a freeze/thaw/freeze step was performed using ethanol/dry ice bath and 37° C. water bath. The tubes were stored at −80° C. until further process of the material. The same process was employed to produce rAAV-GFP, substituting the plasmid pAAV-LRd268 with the plasmid pAAV-GFP (Cell BioLabs Catalog No. AAV-400).

To purify the rAAV-RdCVF1L vector, four 50 mL conical tubes containing the vector from the freeze/thaw/freeze step was thawed at 37° C. in a water bath. Forty microliters of BENZONASE® (Sigma, Catalog No. E8263-25kU) was added to each tube which was then incubated at 37° C. for 30 minutes. The tubes were centrifuged for 10 minutes at 3,000 rpm and the supernatants were transferred into a 500 mL bottle. Six milliliters of a 10% sodium deoxycholate solution (8.2 g in 82 mL water) was added. The sample was briefly mixed and incubated at 37° C. for 30 minutes. The suspension was filtered using 5 µm filters. Subsequently, another filtration step using 0.8 µm filters was performed. A heparin agarose column (8 mL) (Sigma, Catalog No. H6508-25mL) was prepared and the column was equilibrated with 48 mL phosphate buffered saline (PBS) (Invitrogen, Catalog No. 10010-049). The filtered cell lysate was loaded onto the column and the column was washed with 40 mL washing buffer (20 mL 5 M NaCl, 980 mL PBS). The vector was eluted using 15 mL elution buffer (80 mL 5 M NaCl, 920 mL PBS) and collected in a new 50 mL conical tube.

The vector was concentrated by centrifugal filtration. An Amicon Ultra-15 centrifugational filter unit (Millipore, Catalog No. UFC910024) was rinsed once with PBS and the eluted sample was added to the device. Centrifugation was performed in a Beckman Allegro 6KR centrifuge at 2,200 rpm, 22° C., until the sample was concentrated to a 1-2 mL volume. A 15 mL volume of PBS was added and the centrifugation was repeated until the sample volume was ≤1 mL. The purified vector was collected and the filter walls rinsed with 100 µL of PBS. The sample was mixed and 30 µL aliquots of the vector were stored at −80° C. in 600 µL conical tubes until use.

This process was repeated to purify the rAAV-GFP vector.

FIG. 9 and SEQ ID NO:11 show the nucleic acid sequence of the rAAV-RdCVF1L vector.

Genomic Titer Assay of Purified Recombinant AAV Vectors

To measure the genomic titer of the purified rAAV-RdCVF1L and rAAV-GFP vectors, 5 µL of the appropriate vector was mixed with 5 µL 10× DNase buffer, 1 µL DNase I enzyme (Roche, Catalog No. 04716728001), and water for a total volume of 50 µL. After incubation for 30 minutes at 37° C., the enzyme was inactivated by incubation at 65° C. for 10 minutes. Proteinase K (0.5 µL) (Roche, Catalog No, 03115887001) was added. The sample was briefly mixed and incubated for 60 minutes at 50° C. The proteinase K was inactivated by 95° C. for 20 minutes. In parallel, a spike control was used where 5 µL of the spike standard ($2\times10^9$ single stranded DNA from pAAV-GFP) was added to the reaction. These reactions were performed in 0.2 mL 8-tube strips without caps (Biorad, Catalog No. TBS-0201), using 8-flat cap strips (BioRad, Catalog No. TCS-0803), in a BioRad PCR thermo-cycler.

A master mix for the qPCR was setup, containing 825 μL water, 1.875 μL iQ SYBR Green Supermix (BioRad, Catalog No. 170-8882) and 337.5 μL of each of the primers (QPCR CMV 1 (SEQ ID NO:5) and QPCR CMV 2 (SEQ ID NO:6)). A 45 μL volume of the mix was added per well into a 96-well PCR plate, and either 5 μL of the digested vector, spike digested vector, undigested vector (5 μL purified vector with 40 μL water and 5 μL DNase buffer), undigested spiked vector (5 μL purified vector with 35 μL water, 5 μL DNase buffer, and 5 μL spike standard) were added and mixed. A PCR process was performed and samples from Cycle 3 used for melting curve analysis.

The concentration of these single-stranded DNA genomes was analyzed by quantitative PCR as described above. The concentration of the rAAV-RdCVF1L vector particles was determined to be $2\times10^{11}$ vector genome copies per milliliter (GC/mL) and the concentration of rAAV-GFP vector particles was determined to be $2\times10^{11}$ GC/mL.

Silver Stain of Purified Recombinant AAV Vector

To examine the purity of the purified rAAV-RdCVF1L and rAAV-GFP vectors, the vector lysates were subjected to SDS-PAGE with silver staining analysis. Specifically, 20 μL of lysis buffer (8.4 mL water, 500 μL 1 M Tris (pH 8.0), 1 mL Glycerol, 300 μL 5 M NaCl, 50 μL NP-40, 40 μL EDTA, 100 μL PMSF, 1 tablet protease inhibitor (Roche, Catalog No. 11836170001)) was added to 20 μL of the respective purified recombinant AAV vector and kept on ice for 20 minutes. The reaction was centrifuged for 2 minutes at 13,000 rpm and 4° C. in a tabletop centrifuge. The supernatant was transferred into a new tube, 10 μL of 5× reducing sample buffer (Pierce, Catalog No. 39000) was added and the samples were incubated for 10 minutes at 95° C.

Electrophoresis was performed according to the manufacturer's instructions. A 4-15% SDS-PAGE gel was rinsed with water and placed into the gel chamber. Running buffer (1× Tris/Glycine/SDS made by diluting 10× Tris/Glycine/SDS running buffer (BioRad, Catalog No. 161-0732) with water) was added to upper and lower buffer chambers. The wells were rinsed twice with 200 μL running buffer and the samples were loaded. As a control, a 1 μL volume of BENCHMARK™ protein ladder (Invitrogen, Catalog No. 10747-012) was added to the outer wells. Equal concentrations of the vectors, as determined by genomic titer analysis, were loaded. The gel was run at 200 V until the dye reached the bottom of the gel. The gel was fixed and silver stained according to the manufacturer's directions (Biorad Silver Stain Plus, Catalog No. 161-0449).

Only the three AAV virus proteins, VP1 (90 kDa), VP2 (72 kDa), and VP3 (60 kDa) were visible (FIG. 1). Because no other protein bands are visible in the silver stain analysis, this would confirm that the vector preparations resulted in production of highly pure vector particles.

In Vitro Expression of RdCVF1L Mediated by AAV Vector Transduction of ARPE-19 Cells To examine RdCVF1L expression and secretion mediated by the rAAV-RdCVF1L vector, ARPE-19 human retinal pigment epithelial cells (ATCC, Manassas, Va.) were seeded at 200,000 cells in 3 mL of cDMEM per well in a 6-well plate. For the transgene expression after AAV infection, the time limiting step is the second-strand synthesis of the single-stranded DNA genome, which can take several weeks, e.g., see Ferrari et al. (1996). J Virol. 70:3227-3234. However, radiation can be used prior to transduction to expedite the expression of proteins after rAAV vector transduction in cell culture, e.g., see Alexander et al. (1994) J Virol. 68:8282-8287.

Twenty four hours later the cells were irradiated with 175 Gy of $^{137}$Cs with a Shepherd & Associates, Model: Mark I-68 Self-shielded irradiator. Two hours later the medium was replaced with 1.5 mL of fresh cDMEM and 3 μL of purified recombinant AAV vector was added. One plate was untransduced (no AAV) as a control, one plate transduced with rAAV-GFP vector, and one plate was transduced with rAAV-RdCVF1L vector.

Two days after transduction, the supernatants from the transduced and untransduced cells were harvested and filtered through a 0.45 μm filter. An equal volume of lysate buffer (9.4 mL water, 200 μL 1 M Tris (pH 8.0), 40 μL 0.5 M EDTA, 300 μL 5 M NaCl, 100 μL NP-40, 100 μL PMSF, 1 tablet protease inhibitor) was added, and stored at −80° C. until use. The cells from each plate were washed with PBS, scraped off using a cell lifter, pooled and transferred into 15 mL conical tubes. The cells were centrifuged for 4 minutes at 1,200 rpm and 4° C. in a Beckman Coulter Allegra 6KR centrifuge and the supernatant was discarded. The cell pellets were resuspended in 1 mL of lysis buffer (see above), transferred into 1.5 mL tubes, and incubated on ice for 10 minutes. The cell lysates were centrifuged for 2 minutes at 13,000 rpm and 4° C. in a tabletop centrifuge. The cleared cell lysates were aliquoted into 200 μL volumes in 1.5 mL tubes and stored at −80° C. until use.

Western Blot Analysis of Transduced Cell Supernatants and Cell Lysates for RdCVF1L Expression Western blot analysis using a 4-20% SDS-PAGE gel was used to detect RdCVF1L expression using standard techniques. As a control, a 5 μL volume of MAGICMARK™ XP Standard (Invitrogen, Catalog No. LC5602) was added to the outer wells. The gel was run at 200 V until the dye reached the bottom of the gel. Western blot analysis was performed with a Vectastain ABC-Amp Western blot analysis kit by Vector Laboratories, according to a modified version of the manufacturer's instructions. The SDS-PAGE was equilibrated in transfer buffer for 20 min and proteins separated by SDS-PAGE were transferred onto a nitrocellulose membrane using a Trans Blot Semi-Dry Transfer Cell at 20 V for 40 minutes. Once the transfer was completed, the membrane was blocked in 200 mL of 1× casein solution with gentle agitation on a rocker platform for at least two hours at room temperature (RT) for supernatant and 4° C. over night plus 1 hour at RT for cell lysate. The membrane was incubated with 50 mL with rabbit anti-RdCVF protein specific monoclonal antibody (primary antibody, generated by Covance (Denver, Pa.) using purified His-Tag RdCVF1L protein produced in E. coli (Protein One, Rockville, Md.)) diluted 1:2,000 (supernatant) or 1:10,000 (cell lysate) in 1× casein solution with gentle agitation at 4° C. overnight or 2 hours at room temperature, respectively. The membrane was washed with 30 mL of a 1× casein solution 4 times for 5 minutes each at RT with gentle agitation. The membrane was incubated with 30 mL of biotinylated goat anti-rabbit IgG (secondary antibody) diluted 1:24,000 in 1 × casein solution for 1 hour at RT with gentle agitation. The membrane was washed in 30 mL of 1× casein solution 3 times for 5 minutes each at RT with gentle agitation. The membrane was incubated for 45 minutes in Vectastain ABC-AmP in 50 mL of 1× casein containing 100 μL of Reagent A and 100 μL of Reagent B. The membrane was washed in 30 mL of 1× casein solution 3 times for 5 minutes each at RT with gentle agitation.

The membrane was incubated in Tris, pH 9.5. The chemiluminescent signal was acquired using 6 mL of Duolox Substrate (Vector Laboratories, Catalog No. SK 6605) and exposing the membrane to Kodak BioMax MS X-ray film (Kodak Carestream Health, Catalog No. 8572786) in a film cassette for 10 seconds to 5 minutes followed by development of the film using Kodak Developer solution (Kodak GBX, Catalog No. 1900984) and Kodak Fixer solution.

The level of expressed RdCVF1L protein in the cell lysate (FIG. 2A) indicated that the rAAV-RdCVF1L vector transduced ARPE cells efficiently. More importantly, the RdCVF1L protein was efficiently secreted into the cell culture medium of the vector transduced cells (FIG. 2B). However, two RdCVF1L protein positive bands with the expected molecular weight were observed in the rAAV-RdCVF1L vector transduced cell lysate samples (FIG. 2A, lane 3), and three such bands were detected in the cell supernatant samples (FIG. 2B, lane 3). Without wishing to be bound by theory, the two lower molecular weight bands in the cell supernatant (FIG. 2B, lane 3) that have the same molecular weights as those in the cell lysate may have been released from some dead cells in the culture. The third band with slightly higher molecular weight in the supernatant likely represented a secreted form of RdCVF1L which was absent from the cell lysate. The data also suggested that the three forms of RdCVF1L, including the secreted form of RdCVF1L, was likely post-translationally modified.

Summary

The RdCVF1L AAV vector was able to efficiently transduce human retinal pigment epithelial (ARPE-19) cells, leading to expression and secretion of the long RdCVF protein as detected by Western Blot. Two distinct RdCVFL proteins bands were observed in the rAAV-RdCVF1L vector transduced cell lysate samples in addition to a higher band. Three RdCVFL protein bands were detected in the vector transduced cell supernatant. The two of them that having the same molecular weights as those seen in the cell lysate were possibly from dead cells in the cell culture. The third band with slightly higher molecular weight likely represented the secreted form of RdCVF1L. These data also suggested that RdCVF1L, including the secreted form of RdCVF1L, was likely post-translationally modified.

Example 3

In Vivo Expression of RdCVF1 & GFP by AAV Vector in Mouse Eyes

The purpose of this study was to determine whether subretinal administration of rAAV-RdCVF1L can increase RdCVF levels in the retina of the mouse eye. Recombinant AAV serotype 2 vector rAAV-RdCVF1L and control vector rAAV-GFP were prepared as described in Example 2.

Female BALB/C mice, 5-6 weeks of age, were purchased from The Jackson Laboratory (Bar Harbor, Me.) and used in this study. The animals were allowed a minimum 1 week acclimation period prior to use for study. They were housed under a 12-hr light-dark cycle with a light intensity of <50 lux in the cages. Food and water were available ad lib. The experimental design is outlined in Table 1:

TABLE 1

Experimental Design

| Mice (BALB/c) | Eye | Subretinal Injection | Evaluation |
|---|---|---|---|
| N = 7 | Right eye (OD) | rAAV-RdCVF1L | Western blot |
|  | Left eye (OS) | None | Immunohistochemistry |
| N = 7 | Both eyes (OU) | rAAV-GFP |  |

Subretinal injections were performed under anesthesia Animals were anesthetized with an intraperitoneal injection of 25-30 µg/gram of ketamine combined with 5-6 µg/gram xylazine. Anesthetic doses were adjusted to achieve a deep plane of anesthesia. Eyes were treated with a topical application of 0.5% proparacaine hydrochloride (Bausch & Lomb Inc. Rochester, N.Y.) for local anesthesia and 0.3% AK-Tob (Bausch & Lomb Inc.) for disinfection immediately before procedures. Pupils were dilated with 1% tropicamide (Akorn, Inc., Buffalo Grove, Ill.).

Briefly, the anesthetized mouse was positioned under a Zeiss operating microscope with the eye to be injected under view (approx 10× magnification). Gentle pressure was applied on the eyelids with a jeweler's forceps to make the entire globe prolapse forward. The superior temporal conjunctiva was carefully dissected to expose the sclera. A 30-gauge needle was used to perform a shelving puncture of the sclera, choroid and retina at approximately 11 o'clock (right eye) and 1 o'clock (left eye) 0.5 mm posterior to the limbus. A drop of Gonak (2.5%, Akorn, Inc) was instilled on the cornea and a coverslip gently placed on the corneal surface to aid in viewing the fundus. A 33-gauge blunt needle attached to a 5 µL Hamilton syringe was inserted through the sclerotomy in a tangential direction toward the posterior pole without touching the lens and the tip of the needle placed on the inner surface of the retina. The retina was perforated and 1 µL of vector was injected into the subretinal space. After injection, the needle was carefully withdrawn and the conjunctiva repositioned. The success of each injection was confirmed by evaluating the fundus for signs of retinal detachment. Any eyes that displayed subretinal or intravitreal hemorrhages were excluded, as well as eyes that did not display a retinal detachment (or bleb). Neomycin and polymycin B sulfate and Bacitracin Zinc ophthalmic ointment (Bausch & Lomb Inc.) was applied to the cornea to minimize drying of this tissue while the animals were recovering from anesthesia on a warm blanket.

Western Blot Analysis

Western blots were generated with protein extracts from rAAV-RdCVF1L vector injected eyes and contra lateral uninjected control eyes obtained six weeks after administration of rAAV-RdCVF1L vector. Briefly, eyeballs were enucleated and extra-ocular tissues and anterior segment were removed. The remaining posterior segments were quickly frozen with liquid nitrogen. These samples were stored at −80° C. until used for protein extraction. For each eyecup, 200 µL of ice-cold T-PER tissue protein extraction reagent (Pierce, Cat. No. 78510) with Protease Inhibitor Cocktail (Roche Diagnostics, Cat. No. 11836170001) was added. The samples were sonicated 5 seconds on ice with a Sonic dismembrator (Fisher Scientific Model 100, Pittsburgh, Pa.). The sonicated samples were kept on ice for 15 minutes and centrifuged at 10,000 g for 5 minutes at 4° C. to remove cell debris. The supernatants were collected and protein concentrations determined using a Bradford protein assay. For RdCVFL controls, rAAV-RdCVF1L transduced ARPE-19 cell lysate served as the positive control and untransduced cell lysate as the negative control. Proteins were separated by gel electrophoresis. For each lane, 36 µg of total protein was loaded on a 4-20% Criterion™ TGX™ Precast Gel (Bio-Rad, Cat. No. 567-1094) and subjected to electrophoreses at 200 volts for 70 minutes. The proteins were electroblotted onto 0.2 µm nitrocellulose blotting membranes using a Trans Blot Semi-Dry Transfer Cell. The blots were blocked using a 1× casein solution (Vector Laboratories, Cat. No. SP-5020) for 2 hrs at RT and incubated with the rabbit anti-RdCVFL primary antibody (Covance Research Products, Denver, Pa.) diluted 1:2,000 or rabbit anti-opsin, red/green polyclonal antibody (Millipore, Temecura, Calif.) diluted 1:500. After three washes with 1× casein solution each blot was incubated with alkaline phosphatase goat anti-rabbit IgG antibody (Vector Laboratories, Cat. No. AP-1000) diluted 1:3,000. The protein bands were visualized using a chemiluminescent substrate detection kit. Beta-tubulin (50-k(D) was used for equal protein loading control. The blot was stripped with Restore Plus Western Blot Stripping Buffer (Thermo Scientific, Cat. No. 46430) and re-probed with an anti-β-tubulin monoclonal antibody (Sigma-Aldrich, Cat. No. T4026) diluted 1:500 followed by an alkaline phosphatase-conjugated horse anti-mouse IgG antibody (Vector Laboratories, Cat. No. AP-2000) diluted 1:3,000 in 1× casein solution.

Protein densitometry of the autoradiographs, performed with a Kodak Imaging Station, was used to quantify the scanned protein bands, which were normalized with respect to the beta-tubulin level in the same blot.

The presence of RdCVF1L protein was clearly detected in eyes received rAAV-RdCVF1L injection as prominent double immunoreactive bands with a molecular size of approximately 30 kDa (FIG. 3). Western blot of cell lysates from ARPE-19 cells transduced by rAAV-RdCVF1L, which served as a positive control, also yielded 2 individual protein bands with identical sizes. Neither protein extracts from contra lateral eyes which received no subretinal injection, nor eyes injected with rAAV-GFP, produced similar protein bands detected by anti-RdCVFL antibody (FIG. 3). The double immunoreactive bands were similar to the double bands observed in vitro in ARPE-19 cells transduced by rAAV-RdCVF1L. The reason for the absence of the third band (likely the secreted form of RdCVF1L) was that these in vivo samples were protein extracts from retinal cells.

Immunohistochemistry Analysis

RdCVF1L immunostaining was performed in the wholemount preparation of the neuroretina and RPE-choroidasclera. Animals were terminally anesthetized and eyes were enucleated and immediately fixed in 4% paraformaldehyde in phosphate-buffered saline (PBS) 7.4 (1×), liquid (Gibco, Cat. No. 10010-031) overnight at 4° C. Each mouse eye was marked at the inferior quadrant of cornea with India ink prior to enucleation. Eyecups were prepared by removing anterior segment under a Leica dissecting microscope. A small nick was made at the inferior quadrant for orientation. The neuroretina was carefully dissected away from the RPE, severed at the optic nerve. The wholemounts were rinsed three times with 1× PBS, and blocked with 5% donkey serum in 2% Triton X-100 in PBS for 2 hrs at RT. After removing blocking solution, the wholemounts were sequentially incubated with the primary antibody-rabbit anti-RdCVF, 1:1,000 in blocking solution at 4° C. overnight and secondary antibody-ALEXA FLUOR® 488 donkey anti-rabbit 1:1,000 in 2% Triton X-100 in PBS, 2 hrs at RT. After final rinses with PBS, each wholemount was flat-mounted on a glass slide with photoreceptors facing upward for the neuroretina and RPE facing upward for the RPE-choroid-sclera. The flatmounts were then examined with an Olympus BX51 microscope equipped with digital camera (Spot RT Color 2.2.1, Diagnostic Instruments, Inc) and epifluorescence.

Figure 4:
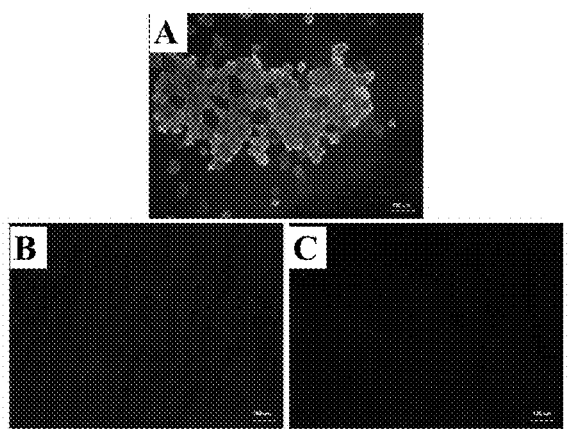
FIG. 4 shows immunohistochemical staining of RdCVF in the RPE cells of RPE-choroid-scleral flatmounts. Robust RdCVF expression was observed in the rAAV-RdCVF1L injected eye of normal Balb/C mice six weeks after vector injection (A), but not in the uninjected contralateral eye (B). No immunoreactivity was seen in the sample processed without primary antibody (C). The flatmounts were counterstained with DAPI to show the cell nuclei in blue.
Figure 5:
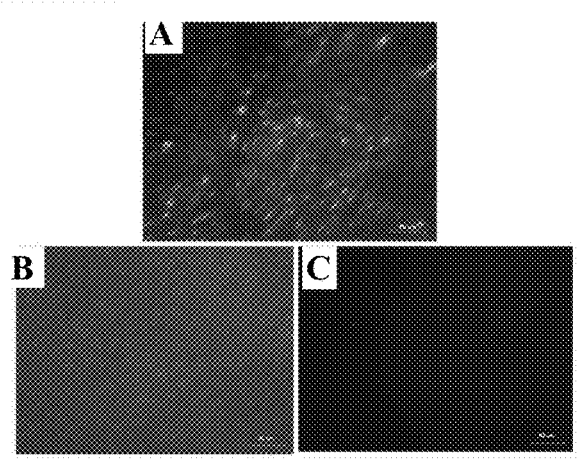
FIG. 5 shows immunohistochemical staining of RdCVF1L of neuroretinal flatmounts. Robust RdCVF1L expression was observed in the photoreceptor cells in the rAAV-RdCVF1L injected eye of normal Balb/C mice six weeks after vector injection (A). The majority of the staining was in the outer segments of photoreceptor cells. In contrast, only background staining was seen in the photoreceptor cells in the uninjected contralateral eye (B). No immunoreactivity was observed in the samples processed without primary antibody (C).

Immunohistochemistry confirmed the increased expression of RdCVF1L protein in the rAAV-RdCVF1L vector injected eyes. Robust RdCVF1L immunostaining was observed in the RPE cells in the rAAV-RdCVF injected eyes (FIG. 4, panel A), but not from the uninjected contralateral eyes (FIG. 4). Increased expression of RdCVF1L was seen only in the focal area, covering approximately one quadrant of each eye, indicating the expression was only confined to the bleb area from subretinal injection. Samples stained without primary antibody did not show any immunoreactivity (FIG. 4, panel C). A marked increase in the expression of this protein was also observed in photoreceptor cells (FIG. 5, panel A) in the rAAV-RdCVF1L injected eyes. Strong RdCVF1L staining was seen in the photoreceptor outer segments in the flatmounted neuroretina. Again, the positive staining was localized only in a focal area of the retina, covering from 10-30% of retina. There was only background staining in the uninjected contra lateral eyes (FIG. 5, panel B). No immunoreactivity was found in the samples processed without primary antibody (FIG. 5, panel C).

GFP Expression in Mouse Eyes

To determine whether the tested AAV vectors could efficiently transduce RPE and photoreceptor cells in mouse eyes, a group of mice (n=7) were injected subretinally with rAAV-GFP and sacrificed 6 wks later. RPE-choroid-sclera and neuroretina were separated and flat-mounted on glass slides. Fluorescent microscopy revealed robust GFP expression in RPE and photoreceptor layer (data not shown). The RPE cells expressing GFP spread 1-2 quadrants of the flatmount, with the maximal number and most robust GFP-expressing cells present at the injection site. Transduced RPE cells appeared healthy as they maintained their hexagonal morphology. In the flatmounted neuroretinas, GFP expression was identified in the photoreceptor outer segments. Occasionally inner retinal cells, such as ganglion cells, were GFP positive, possibly due to vector leakage into the vitreous after subretinal injection.

Summary

This study demonstrated efficient transduction of RPE and photoreceptor cells by the rAAV-RdCVF1L vector following successful subretinal injection. The RdCVF1L expression construct delivered by this vector led to significant increases in the levels of RdCVF1L protein in the mouse eyes.

Example 4

Effect of Long Form RdCVF Expression Mediated by Adeno-Associated Viral Vector on Photoreceptor Survival in rd10 Mouse Eyes The purpose of this study was to determine whether subretinal administration of an AAV based gene therapy vector encoding RdCVF1L could promote photoreceptor survival in rd10 mice, a naturally occurring animal model for human inherited retinal degeneration. Rd10 mice are a naturally occurring animal model for autosomal recessive retinitis pigmentosa (RP). Rd10 mice have a missense point mutation in rod cGMP phosphodiesterase gene, resulting in apoptosis of photoreceptor cells (Chang et al. (2007) *Vision Res* 47:624-633). Rod photoreceptor cells start degenerating at 18 days of age, with peak photoreceptor death occurring at P25 (Gargini et al. (2007) *J Comp Neurol* 500:222-238). By five weeks most photoreceptor cells have been degenerated (Chang et al. (2002) *Vision Res* 42:517-525; Chang et al. (2007) *Vision Res* 47:624-633; Gargini et al. (2007) *J Comp Neurol* 500:222-238). Interestingly, it has been found that rearing rd10 mice in darkness slows photoreceptor degeneration by as much as four weeks (Chang et al. (2007) *Vision Res* 47:624-633), suggesting light exposure can accelerate photoreceptor death. On the other hand, delayed photoreceptor degeneration by keeping these mice in darkness can extend the therapeutic time window for vectors that need to time for therapeutic transgene expression, e.g., adequate transgene expression from an AAV will usually take about 3 weeks.

Breeding pairs of congenic inbred strain of rd10 mice, 4-5 weeks of age, were purchased from The Jackson Laboratory (Bar Harbor, Me.) and bred in an animal facility. They were housed under a 12-hr light-dark cycle with a light intensity of <50 lux in the cages. Food and water were available ad lib. After the surgery, as described below, the pups with their mothers were kept in darkness until they were weaned at the age of 3 weeks. Then all animals were transferred back to the previous room with 12-hr light-dark cycle. The experimental design is Table 2.

TABLE 2

Experimental Design

| Mice (rd10) | Eye | Subretinal Injection | Evaluation |
|---|---|---|---|
| N = 12 | OD | rAAV-RdCVF1L | Retinal histology |
|  | OS | None | Cone morphology/number |

Animals (at the age of postnatal day 3) were anesthetized by hypothermia. This anesthetic method has been well established for neonatal mice and rats for up to 5 days of age and is appropriate for short, minor surgical procedures (5-15 minutes) in these animals (Gaertner et al. Anesthesia and Analgesia 2nd ed. pages 277-278). The pup was placed on crushed ice for 3-4 minutes. During this time the color of pup was changed from pink to pale. Subretinal injections were performed under this type of anesthesia.

The anesthetized mouse was positioned under a Zeiss operating microscope with the eye to be injected under view (approx. 10× magnification). Eyelids and adjacent area were disinfected with 5% povidone-iodine. The eye was exposed by separation of the palpebral fissure using an Iris scissor. Gentle pressure was applied on the eyelids with a jeweler's forceps to make the entire globe prolapse forward. A drop of 0.3% Tobromycin (Bausch & Lomb Inc.) was given for disinfection. A 30-gauge sharp needle was used to perform a shelving puncture of the sclera, choroid and retina at approximately the 11 O'clock (right eye) position about 0.5 mm posterior to the limbus. A 33-gauge blunt needle attached to a 5-µL Hamilton syringe was inserted through the sclerotomy in a tangential direction toward the posterior pole. The tip of the needle was placed in the subretinal space, and 1 µL of AAV vector was injected into the subretinal space. After injection, the needle was slowly withdrawn. Any eyes that displayed subretinal or intravitreal hemorrhages were excluded from study. Neomycin and polymycin B sulfate and bacitracin zinc ophthalmic ointment (Bausch & Lomb Inc.) was applied to the cornea to prevent infection and minimize drying of this tissue. Animals were allowed to recover on a warm heating pad.

Retinal Histology

Mice were deeply anesthetized and their eyes were marked at the superior quadrant with red tissue dye for orientation. They were then sacrificed and immediately enucleated and fixed in Davidson's fixative for about 24 hrs at RT. After sequential dehydration in ethanol and Clear-rite, eyes were embedded in paraffin (Fisher Sci., Houston, Tex.). Retinal sections of 5 µm thickness were cut along the vertical meridian to allow examination of the superior and inferior retina. The sections were stained with hematoxylin and eosin and examined under a light microscope (Olympus BX51). The outer nuclear layer (ONL) thickness was evaluated by counting the number of rows of nuclei in the central and peripheral retina. Photoreceptor morphology was also examined.

Figure 7:
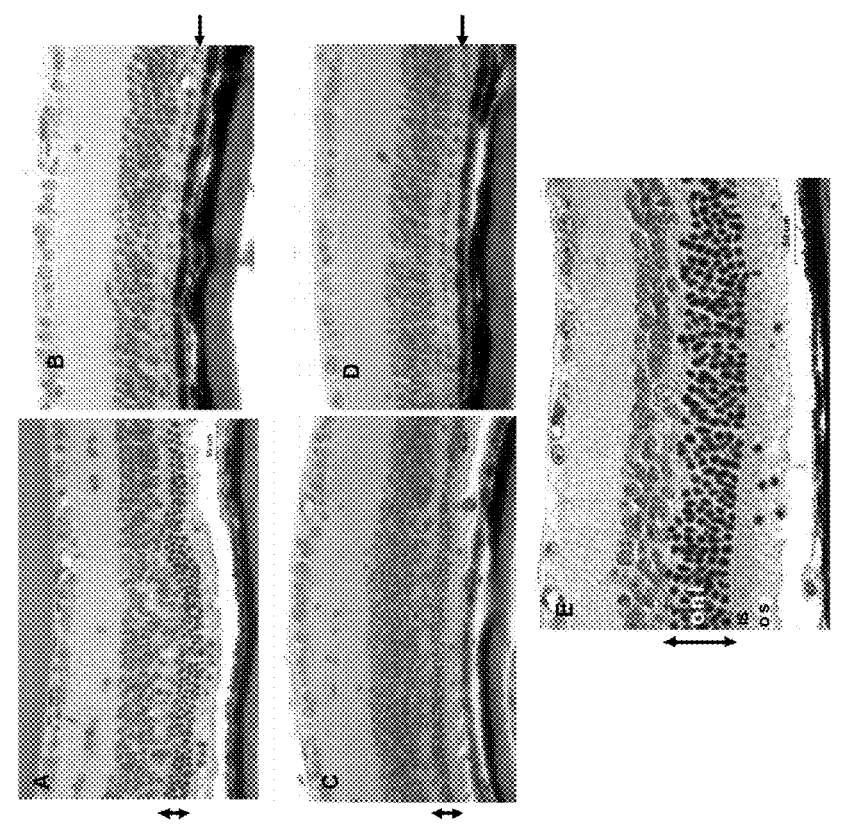
FIG. 7 shows photoreceptor rescue by subretinal injection of AAV-RdCVF1L in rd10 mice. Light photomicrographs of representative retinal sections from 2 mice in which the right eyes received rAAV-RdCVF1L at postnatal day 3 (A and C) and left eyes (B and D) serve as untreated controls. The rd10 mice were sacrificed at 5 weeks old. Note the difference in the outer nuclear layer (ONL) thickness between treated (double head arrows) and untreated eyes (single head arrows). There are 2-4 rows in AAV-RdCVF treated eyes (A and C) versus 1 row in untreated eyes (B and D). Photoreceptor inner and outer segments remained in some areas of the protected retina (E). IS, inner segments; OS, outer segments; ONL, outer nuclear layer.

The treated rd10 mouse eyes were assessed for the degree of structural rescue at the age of 5 weeks. Light microscopy showed obvious preservation of outer nuclear layer (ONL) in the AAV-RdCVF1L treated eyes in comparison with untreated contralateral eyes. Typically, the RdCVF1L vector-treated retina possessed 2-5 rows of photoreceptor nuclei in the superior and/or inferior regions as opposed to 1-2 rows in the untreated, contralateral eyes in the same locations (FIG. 7). The rescue was not limited to the injected area, the superior quadrant, as the protection was also observed in the inferior quadrant. Morphometric analysis showed approximately 75% of retina was protected in vector-treated eyes in comparison with 34% in untreated eyes. Some preserved photoreceptors even possessed inner and outer segments (FIG. 7E). It is noteworthy that the rescued photoreceptors contained both rod and cone cells.

Cone Photoreceptor Staining and Counting

Peanut agglutinin (PNA), a cone cell-specific marker, was used to stain the wholemount preparation of the retina. Mouse eyes were marked at the superior quadrant of cornea with Indian ink and red dye at temporal quadrant prior to enucleation. They were immediately fixed in 4% paraformaldehyde at least overnight at 4° C. Eyecups were prepared by removing anterior segment under a Leica dissecting microscope. A small nick was made at the superior quadrant for orientation. After 4 radial cuts around the circumference, the entire neuroretina was carefully dissected away from the eye cup. The retinas were rinsed three times with 1× PBS, and blocked with 6% of bovine serum albumin (BSA) in PBS (Gibco, Cat. No. 10010-031) with 0.2% Triton-X 100 for 30 minutes at RT. After removing blocking solution, retinas were incubated with Lectin PNA Conjugates Alexa Fluor 594 (1:250 in PBS, Invitrogen Corp, Chicago, Ill.) overnight at 4° C. After final rinses with PBS, each retina was flat-mounted on a glass slide with photoreceptors facing upward. The retinal wholemounts were then examined with an Olympus BX51 microscope equipped with digital camera (Spot RT Color 2.2.1, Diagnostic Instruments, Inc) and epifluorescence.

To assess cone cell density in the retinal wholemounts, two images were taken with 60× objective from each retinal quadrant at 1 and 2 mm location from the edge of optic nerve head, respectively. The number of cones presented each image (390×293 µm) were counted with the Image Pro Plus software (Media Cybernetics, Inc. Bethesda, Md.).

For some eyes, retinal cryostat sections (12 µm in thickness) were cut with a Leica cryostat microtome (Leica Microsystems, Model CM 1850, Leica, Bannockburn, Ill.) and stained with PNA, examined with the fluorescent microscope aforementioned.

Cone photoreceptor cells were identified by PNA labeling, which selectively stains cone inner and outer segments, in flat-mounted neuroretina. Fluorescent microscopy showed severe degeneration of cone cells in the untreated eyes, particularly at the posterior central retina, e.g., around the optic nerve head. Cone cells lost outer segments, and their inner segments are short, blunted and irregular. In contrast, vector-treated eyes had greater cone density, much less disorganized cone segments, and more uniformed cone staining (data not shown). Under higher magnification, PNA-positive cone cells were counted in all 4 quadrants at 1 and 2-mm locations from optic nerve head. Quantification of cone density showed significantly high numbers of cone photoreceptors in the vector-treated eyes relative to untreated, contralateral ones: 181+/−46.4 versus 50+/−25.2 cones/0.114 mm$^2$, p=0.001.

RdCVF Immunohistochemistry

RdCVF immunostaining was performed in the wholemount preparation of the neuroretina and RPE-choroida-sclera. The wholemounts were rinsed three times with 1× PBS, and blocked with 5% donkey serum and 2% Triton X-100 in PBS for 2 hrs at RT. After removing blocking solution, the wholemounts were sequentially incubated with the primary antibody-rabbit anti-RdCVF at 1:1,000 in blocking solution at 4° C. overnight and secondary antibody-Alexa Fluor® 488 donkey anti-rabbit at 1:1,000 and 2% Triton X-100 in PBS, 2 hrs at RT. After final rinses with PBS, each wholemount was flat-mounted on a glass slide with photoreceptors facing upward for the neuroretina and RPE facing upward for the RPE-choroid-sclera. The flat-mounts were then examined with an Olympus BX51 microscope equipped with a digital camera (Spot RT Color 2.2.1, Diagnostic Instruments, Inc) and epifluorescence.

Figure 6:
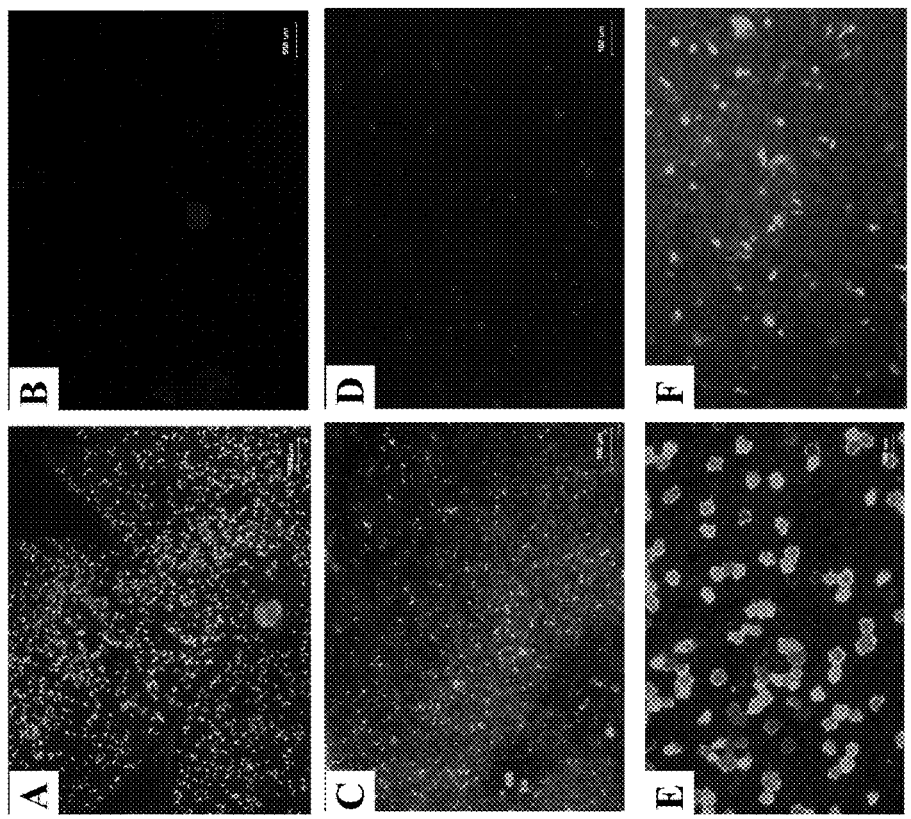
FIG. 6 shows results for studies that demonstrated RdCVF1L expression in RPE and photoreceptor cells 5 weeks after subretinal injection of AAV-RdCVF1L in rd10 mice. RdCVF-expressing RPE cells were seen in approximately half of RPE-choroid-scleral flatmount of rAAV-RdCVF1L vector injected eye (A), but not in the uninjected, contralateral eye (B). Photoreceptor cells (C) were also transduced as RdCVF-expressing segments were observed in the flat-mounted retina of the same eye. In contrast, no RdCVF-expression was found in the uninjected, contralateral eye (D). The dark green cells in (D) likely are autofluorescent macrophages adhered to the retina. High magnification view of transduced RPE cells (E), maintaining typical hexagonal morphology, and RdCVF-expressing photoreceptor segments (F).

Robust RdCVF immunoreactivity was observed in the RPE cells in 5 out of 6 rAAV-RdCVF1L injected eyes (a representative example from one eye is seen in (FIG. 6A), but not from the uninjected contralateral eyes (FIG. 6B). One eye that received rAAV-RdCVF1L injection was excluded from analysis due to microphthamia. Efficient expression of RdCVF1L was seen in the focal area, spreading approximately 1.5 to 3 quadrants of each eye. RdCVF1L-expressing RPE cells maintained typical hexagonal morphology (FIG. 6E), suggesting there was no obvious negative impact on the RPE from the vector administration or the RdCVF1L expression. Similarly to RPE expression of RdCVF1L, efficient expression in the immunoreactivity of this protein was also observed in neuroretina in the rAAV-RdCVF1L injected eyes (FIG. 6C). There was no staining in the uninjected, contralateral eyes (FIG. 6D). Strong RdCVF1L staining was clearly seen in the photoreceptor cells in 3 out of 5 eyes, particularly in the inner/outer segments (FIG. 6F). Lack of RdCVF immunoreactivity in the other 2 eyes may be attributed to photoreceptor degeneration. Again, the positive staining was localized only in a focal area of the retina. The observation that no detectable expression of RdCVF1L in the uninjected contralateral eyes suggests that the level of endogenous RdCVF1L may be lower that the limit of detection by immunohistochemical staining.

Summary

This study demonstrated subretinal injection of rAAV-RdCVF1L vectors led to efficient transduction of the RPE and photoreceptor cells and robust RdCVF1L protein expression in the rd10 mouse eyes. More importantly, this vector prolonged both rod and cone photoreceptor survival and improved cone morphology in this clinically relevant animal model of retinitis pigmentosa (RP).

Example 5

Figure 8:
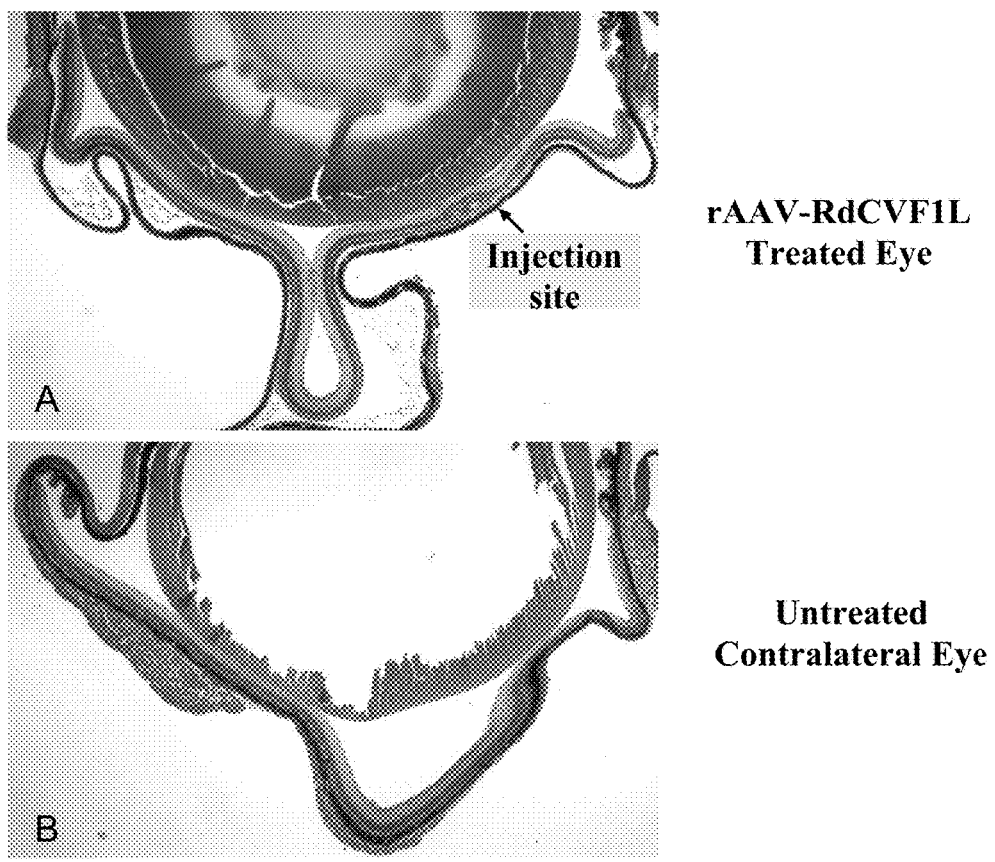
FIG. 8 shows a light photomicrograph of an eyecup from a representative 5-week old rd10 mouse that received a subretinal injection of rAAV-RdCVF1L in one eye (Panel A, FIG. 8) and no treatment in the contralateral eye (Panel B, FIG. 8). As shown, more photoreceptor cells were preserved in the treated eye.

Subretinal Injection of rAAV-RdCVF1L Preserved Photoreceptor Cells Distant From the Injection Site in rd10 Mice To examine if rescue of photoreceptor cells by rAAV-RdCVF1L can extend to the areas distant from the injection site, rAAV-RdCVF1L (1 µL, 2×10$^8$ GC) was subretinally injected into the superior quadrant of rd10 mouse right eyes at postnatal day 3, with the uninjected contralateral eyes as controls. Mice were sacrificed at 5-weeks old. Retinal histology from the entire eye cup was examined FIG. 8 shows a light photomicrograph of an eyecup from a representative 5-week old rd10 mouse that received a subretinal injection of rAAV-RdCVF1L in one eye (Panel A, FIG. 8) and no treatment in the contralateral eye (Panel B, FIG. 8). Note the difference in ONL thickness between the treated and untreated eye. Photoreceptor preservation was clearly seen in the entire retina of rAAV-RdCVF1L treated eye (Panel A, FIG. 8). The injection site in the superior retina was labeled. In contrast, most photoreceptor cells were lost except in the inferior peripheral retina in the untreated contralateral eye (Panel B, FIG. 8).

Example 6

Subretinal Injection of rAAV-RdCVF1L Preserved Rod Photoreceptor Cells

To examine if the rod photoreceptor cells can be rescued (in addition to cone photoreceptor cells) by rAAV-RdCVF1L, the right eyes of rd10 mouse at postnatal day 3 were subretinally injected with rAAV-RdCVF1L (1 µL, 2×10$^8$ GC), with the uninjected contralateral eyes as controls. Mice were sacrificed at 5-weeks old. Retinal tissue was subjected to rhodopsin immunohistochemical staining The sections were counterstained with DAPI (diamidino-2-phenylindole, blue color) to aid in identification of retinal layers.

Robust expression of rhodopsin was observed in both the segment layer and nuclear layer of photoreceptor cells in the rAAV-RdCVF1L treated eye (data not shown). However, only a few cells showed rhodopsin staining in the untreated eye (data not shown).

Example 7

Functional Rescue of Photoreceptors by RdCVFL Mediated by Adeno-Associated Viral Vectors in Rd10 Mice The purpose of this study was to assess the protective effect of RdCVF delivered by AAV vector on retinal function and structure in the rd10 mice. Neonatal rd10 mice, at 3 or 4 days of age, were injected subretinally with rAAV-RdCVFL vector in one eye while the contralateral eye was left untreated. Five weeks after subretinal injection the mice were tested with electroretinogram (ERG) to evaluate retinal functions. After ERGs, the mice were sacrificed, and their eyes were processed for histological assessment of the retina.

Recombinant AAV serotype 2 vector rAAV-RdCVF1L and control vector rAAV-GFP were prepared as described in Example 2.

Breeding pairs of congenic inbred strain of rd10 mice, 4-5 weeks of age, were purchased from The Jackson Laboratory (Bar Harbor, Me.) and bred at our animal facility. They were housed under a 12-hr light-dark cycle with a light intensity of <50 lux in the cages. Food and water were available ad lib. After the surgery, the pups with their mothers were kept in darkness until they were weaned at the age of 3 weeks. Then all animals were transferred back to the previous room with 12-hr light-dark cycle. The experimental design is outlined in Table 3.

TABLE 3

| Mice (rd10) | Eye | Subretinal Injection | Evaluation |
|---|---|---|---|
| N = 13 | OD | rAAV-RdCVF1L | ERG |
| | OS | None | Retinal histology |

Animals were anesthetized and subretinal injection was performed as described above in Example 4.

Mice were dark adapted overnight (at least 14 hours) before the experiments and their pupils dilated with 0.5% tropicamide (Alkorn) eye drops. Anesthesia was induced by intraperitoneal injection of ketamine and xylazine. Silver needle electrodes served as reference (forehead) and ground (tail) and DTL ring electrodes as active electrodes. Gonesol was applied to ensure good electrical contact and to keep the eye hydrated during the entire procedure. The recording setup featured a Ganzfeld bowl, a DC amplifier, and a computer-based control and recording unit of the Espion E3 electroretinography system (Diagnosys LLC, Lowell, Mass.). ERGs were recorded from both eyes simultaneously after the mice were placed in the Ganzfeld bowl. Single-flash and flicker recordings were obtained both under dark-adapted (scotopic) and light-adapted (photopic) conditions. Single flash stimuli were presented with increasing intensities, reaching from $10^{-2}$ to 25 cds/m$^2$. Five responses were averaged with an inter-stimulus interval of 5 or 17 seconds. Flicker stimuli had an intensity of 3 cds/m$^2$ with frequencies of 2, 5, 10, 15, and 30 Hz. Light adaptation was performed with a background illumination of 30 cds/m$^2$ presented for 10 minutes to reach a stable level of the photopic responses. For comparison of the mean amplitudes, Student pair-t-test was used.

Mice were deeply anesthetized and marked their eyes at the superior quadrant with red tissue dye for orientation. They were then sacrificed and immediately enucleated and fixed in Davidson's fixative for about 24 hrs at room temperature. After sequential dehydration in ethanol and Clear-rite, eyes were embedded in paraffin (Fisher Sci., Houston, Tex.). Retinal sections of 5 μm thickness were cut along the vertical meridian to allow examination of the superior and inferior retina. The sections were stained with hematoxylin and eosin and examined under a light microscope (Olympus BX51). The outer nuclear layer (ONL) thickness was evaluated by counting the number of rows of nuclei in the central and peripheral retina. Photoreceptor morphology was also examined.

Results
Rescue of Retinal Function in rAAV-RdCVF1L-Treated Eyes

Figure 10A:
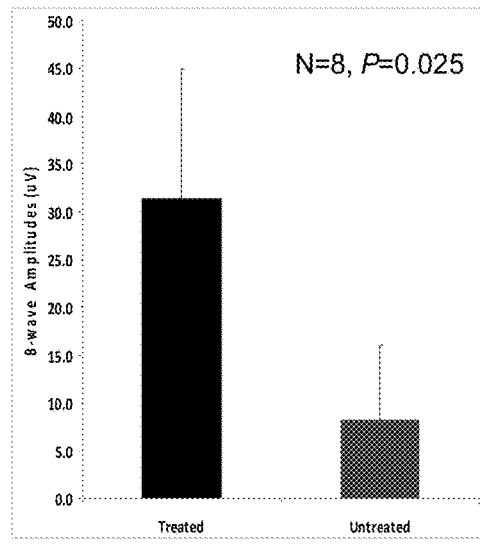
FIG. 10A: rAAV-RdCVF1L delivery improves retinal function in the rd10 mice. The ERGs were performed at approximately 5 wks after injection of rAAV-RdCVF1L. Measurements of ERG responses from all 8 mice we tested show that the mean b-wave amplitudes from treated eyes were about 3 times greater than those of untreated fellow eyes, which was statistically significant (p=0.025).
Figure 10B:
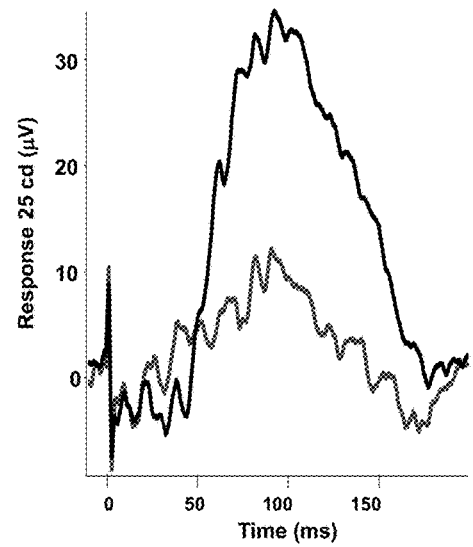
FIG. 10B: rAAV-RdCVF1L delivery improves retinal function in the rd10 mice. The ERGs were performed at approximately 5 wks after injection of rAAV-RdCVF1L. Right panel: These are average of eight waveforms from the treated eye (black line, n=8) and untreated fellow eyes (red line, n=8) which were recorded at the 25 cd.s/m$^2$ intensity of single light flashes under the dark background. Obviously, the treated eyes had a much higher response than the fellow eyes. Left panel: Measurements of ERG responses from all 8 mice we tested show that the mean b-wave amplitudes from treated eyes were about 3 times greater than those of untreated fellow eyes, which was statistically significant (p=0.025).

As expected, at the age of 5 weeks, the rd10 mice showed a significant reduction of scotopic and photopic responses in ERG recording in comparison to the age-matched, wild-typed C57BL/6 mice (data not shown). However, in the rd 10 mice (n=8) the eyes treated with rAAV-RdCVF1L showed an approximately 3-fold increase in b-wave amplitudes (33.6±14 μV) as compared to the untreated fellow eyes (11.5±8.4 μV) under the flash intensity of 25 cd at the scotopic background (FIGS. 10A and 10B). Under this condition, both rod and cone responses were recorded. Statistical analyses indicate significant differences in ERG amplitudes between rAAV-RdCVF1L treated eyes and the control eyes (p=0.025). Some animals (n=5) were excluded from ERG testing (excluded before ERG testing) due to corneal opacity, cataract or microphthalmia likely resulting from intraocular surgery at the neonatal period.

Figure 11A:
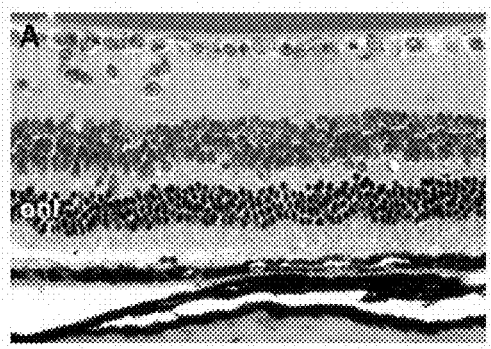
FIGS. 11A and 11B: Photoreceptor preservation by subretinal injection of rAAV-RdCVF1L in rd10 mice. Light photomicrographs of representative retinal sections from a mouse in which right eye received rAAV-RdCVF1L at postnatal day 3 (A) and left eye (B) serving as untreated controls. Note the difference in ONL thickness between treated and untreated eye. There are about 4 rows in the treated eye (A) versus 1 row in untreated eyes (B). Photoreceptor outer segments are remained in some areas of the protected retina; onl, outer nuclear layer.
Figure 11B:
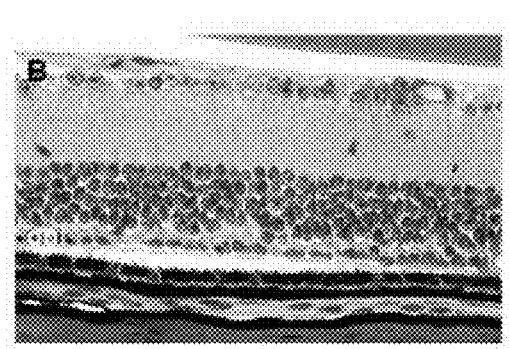
Figure 12:
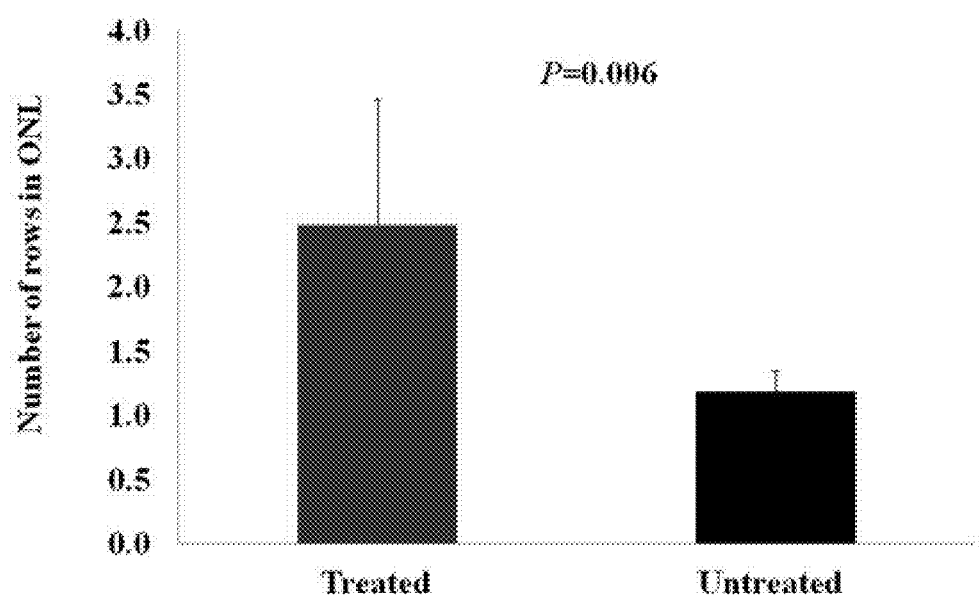
FIG. 12: Comparison of the thickness of outer nuclear layer (ONL) in rAAV-RdCVF1L treated versus untreated eyes in rd10 mice. The average thickness of ONL in the treated eyes (red bar) is significantly greater (P=0.006) than that in untreated eyes (black bar). Numbers represent mean+SD.

Structural Preservation of Photoreceptors in rAAV-RdCVF1L-Treated Eyes:

To determine whether the increased ERG responses in rAAV-RdCVF1L treated eyes correlate with structural preservation of photoreceptor cells in the rd10 mice, animals were sacrificed immediately after ERG. Their eyes were processed for histological evaluation. Light microscopy showed obvious preservation of outer nuclear layer (ONL) in the AAV-RdCVFL treated eyes in comparison with untreated contralateral eyes. Typically, the vector-treated retina possessed 2-4 rows of photoreceptor nuclei in the superior and/or inferior regions as opposed to 1-2 rows in the untreated, contralateral eyes (FIGS. 11A and 11B). The photoreceptor preservation was not limited to the injected area—the superior quadrant as the protection was also observed in the inferior quadrant. Some preserved photoreceptors even possessed inner and outer segments. Morphometric analyses show a significant increases in the number of rows of ONL in treated eyes (2.5+1.0) in comparison with that in the control eyes (1.2+0.2) (p=0.006) (FIG. 12).

Summary

ERG demonstrated a significant increase in the amplitudes of b-wave in rAAV-RdCVF1L-treated eyes (33.6±14 μV) in relative to the untreated fellow eyes (11.5±8.4 μV). The increase in the ERG amplitudes was correlated with improvement of retinal structure. This study demonstrated subretinal injection of rAAV-RdCVF1L vectors significantly improved retinal function and delayed photoreceptor degeneration in the Rd10 mice.

---

What is claimed is:

1. A polynucleotide comprising a nucleotide sequence encoding a rod-derived cone viability factor (RdCVF) protein operatively linked to a second nucleotide sequence encoding an N-terminal signal sequence,
   wherein the RdCVF coding sequence comprises a recoded nucleotide sequence in which at least one native codon is changed to a different codon that encodes for the same amino acid as the native codon;
   the RdCVF protein is a human RdCVF protein;
   and the N-terminal signal sequence is an Igk signal sequence.

2. The polynucleotide of claim 1, wherein the RdCVF protein is an RdCVF1 protein.

3. The polynucleotide of claim 1, wherein the RdCVF protein is an RdCVF2 protein.

4. The polynucleotide of claim 1 where in the RdCVF protein is a short version RdCVF protein.

5. The polynucleotide of claim 1, wherein the RdCVF protein is a long version RdCVF protein.

6. The polynucleotide of claim 1, wherein the RdCVF protein is human RdCVF1-long.

7. The polynucleotide of claim 1, wherein the coding sequence for the RdCVF protein comprises nucleotides 106 to 741 of SEQ ID NO:1, nucleotides 106 to 429 of SEQ ID NO:1, nucleotides 106 to 432 of SEQ ID NO:3 or nucleotides 106 to 744 of SEQ ID NO:3.

8. The polynucleotide of claim 1, wherein the second nucleotide sequence comprises nucleotides 1-105 of SEQ ID NO:1.

9. The polynucleotide of claim 1, wherein the second nucleotide sequence codes for an amino acid sequence comprising SEQ ID NO:15, amino acids 2-34 of SEQ ID NO:2, or amino acids 7-21 of SEQ ID NO:2.

10. The polynucleotide of claim 1, wherein the recoded RdCVF nucleotide sequence has at least 40% of the codons recoded.

11. The polynucleotide of claim 1, wherein the recoded RdCVF nucleotide sequence has at least 15% of the nucleotides different as compared to a corresponding native nucleotide sequence.

12. The polynucleotide of claim 1, wherein the recoded RdCVF nucleotide sequence is less than 90% identical to a corresponding native nucleotide sequence.

13. The polynucleotide of claim 1, wherein the recoded RdCVF nucleotide sequence has one or more of the characteristics selected from the group consisting of no procarya inhibitory motifs, no consensus splice donor sites, no cryptic splice donor sites and the GC content is between 60-65%.

14. The polynucleotide of claim 1 comprising SEQ ID NO: 11; the nucleotide sequence of 150-2080 of SEQ ID NO: 11; or the nucleotide sequences of 150-812, 820-1312 and 1340-2080 of SEQ ID NO: 11.

15. A viral vector comprising the polynucleotide of claim 1.

16. The viral vector of claim 15, wherein the viral vector is an adeno-associated viral (AAV) vector.

17. The viral vector of claim 16, wherein the AAV vector is AAV serotype 2.

18. The viral vector of claim 16, wherein the AAV vector is AAV serotype 8.

19. An isolated cell comprising the polynucleotide of claim 1, wherein the cell secretes the RdCVF protein.

20. An RdCVF protein produced by the cell of claim 19, wherein the protein is not a naturally occurring protein.

21. A method of preserving ocular cells in the eye of a mammal, wherein the ocular cells are selected from the group consisting of ocular rod cells and ocular cone cells, comprising administering to the eye of the mammal the polynucleotide of claim 1, the viral vector of claim 15 or the RdCVF protein of claim 20, in an amount effective to preserve the ocular cells.

22. The method of claim 21, wherein the viral vector or the polynucleotide is administered by subretinal injection.

23. The method of claim 21, wherein the viral vector or the polynucleotide is administered by intravitreal injection, injection to the intraanterior chamber of the eye, subconjunctival injection or subtenon injection.

24. The method of claim 21, wherein the mammal is a human.

25. The method of claim 21, wherein the mammal suffers from an ocular disease selected from the group consisting of a retinal dystrophy, Stargardt's disease, retinitis pigmentosa, dry age-related macular degeneration (dry AMD), geography atrophy (advanced stage of dry AMD), wet age-related macular degeneration (wet AMD), glaucoma/ocular hypertension, diabetic retinopathy, Bardet-Biedel syndrome, Bassen-Kornzweig syndrome, Best disease, choroidema, gyrate atrophy, congenital amaurosis, refsum syndrome, Usher syndrome, thyroid related eye disease, Grave's disease, a disease associated with retinal pigmented epithelial cells, anterior segment disease, lens disease/cataracts, an eye cup disorder, and uveitis.

26. A method of preserving ocular cells in the eye of a mammal, wherein the ocular cells are selected from the group consisting of ocular rod cells and ocular cone cells,
   comprising administering to the eye of the mammal the polynucleotide of claim 1 or the viral vector of claim 15, wherein the polynucleotide or the viral vector is administered by subretinal injection and the ocular cells are preserved at a site at least 1 mm from the site of subretinal injection.

* * * * *

SEQUENCE LISTING

```
<160> NUMBER OF SEQ ID NOS: 15

<210> SEQ ID NO 1
<211> LENGTH: 741
<212> TYPE: DNA
<213> ORGANISM: Artificial Sequence
<220> FEATURE:
<223> OTHER INFORMATION: Igk signal peptide sequence and recoded rdCVF1L
      coding sequence (-ATG)

<400> SEQUENCE: 1
atggagacag acacactcct gctatgggta ctgctgctct gggttccagg ttccactggt      60
gacgcggccc agccggccag gcgcgccgta cgaagcttgg tacccgccag cctgttcagc    120
ggccggatcc tgatcaggaa caacagcgac caggacgagc tggacaccga ggccgaagtg    180
```

```
agcaggaggc tggagaacag actggtgctg ctgttctttg gcgccggagc ctgccctcag    240
tgccaggcct tcgtgcccat cctgaaggat ttctttgtga ggctgaccga cgagttctac    300
gtgctgagag ccgcccagct ggccctggtg tatgtgagcc aggacagcac cgaggagcag    360
caggacctgt tcctgaagga catgcccaag aagtggctgt tcctgccctt cgaggacgac    420
ctgagaagag acctgggcag gcagttcagc gtggagagac tgcccgccgt ggtggtgctg    480
aagcctgatg gcgacgtgct gaccagagat ggcgccgacg agatccagag actgggcacc    540
gcctgcttcg ccaactggca ggaggccgcc gaggtcctgg acagaaactt ccagctgccc    600
gaggatctgg aggatcagga gcccagatcc ctgaccgagt gcctgaggcg cacaagtac     660 agagtggaga aggccgccag aggcggcaga ccctggcg gcggaggagg agaggagggc     720
ggagccggcg gactgttctg a                                              741
```

<210> SEQ ID NO 2
<211> LENGTH: 246
<212> TYPE: PRT
<213> ORGANISM: Artificial Sequence
<220> FEATURE:
<223> OTHER INFORMATION: recoded RdCVF1L with Igk signal peptide
      sequence (-Met)

<400> SEQUENCE: 2

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Val Arg Ser
            20                  25                  30

Leu Val Pro Ala Ser Leu Phe Ser Gly Arg Ile Leu Ile Arg Asn Asn
        35                  40                  45

Ser Asp Gln Asp Glu Leu Asp Thr Glu Ala Glu Val Ser Arg Arg Leu
    50                  55                  60

Glu Asn Arg Leu Val Leu Leu Phe Phe Gly Ala Gly Ala Cys Pro Gln
65                  70                  75                  80

Cys Gln Ala Phe Val Pro Ile Leu Lys Asp Phe Phe Val Arg Leu Thr
                85                  90                  95

Asp Glu Phe Tyr Val Leu Arg Ala Ala Gln Leu Ala Leu Val Tyr Val
            100                 105                 110

Ser Gln Asp Ser Thr Glu Glu Gln Asp Leu Phe Leu Lys Asp Met
        115                 120                 125

Pro Lys Lys Trp Leu Phe Leu Pro Phe Glu Asp Asp Leu Arg Arg Asp
    130                 135                 140

Leu Gly Arg Gln Phe Ser Val Glu Arg Leu Pro Ala Val Val Leu
145                 150                 155                 160

Lys Pro Asp Gly Asp Val Leu Thr Arg Asp Gly Ala Asp Glu Ile Gln
                165                 170                 175

Arg Leu Gly Thr Ala Cys Phe Ala Asn Trp Gln Glu Ala Ala Glu Val
            180                 185                 190

Leu Asp Arg Asn Phe Gln Leu Pro Glu Asp Leu Glu Asp Gln Glu Pro
        195                 200                 205

Arg Ser Leu Thr Glu Cys Leu Arg Arg His Lys Tyr Arg Val Glu Lys
    210                 215                 220

Ala Ala Arg Gly Gly Arg Asp Pro Gly Gly Gly Gly Glu Glu Gly
225                 230                 235                 240

Gly Ala Gly Gly Leu Phe
            245
```

<210> SEQ ID NO 3
<211> LENGTH: 744
<212> TYPE: DNA
<213> ORGANISM: Artificial Sequence
<220> FEATURE:
<223> OTHER INFORMATION: Igk signal peptide sequence and recoded RdCVF1L coding sequence (+ATG)

<400> SEQUENCE: 3

```
atggagacag acacactcct gctatgggta ctgctgctct gggttccagg ttccactggt    60
gacgcggccc agccggccag gcgcgccgta cgaagcttgg tacccatggc cagcctgttc   120
agcggccgga tcctgatcag gaacaacagc gaccaggacg agctggacac cgaggccgaa   180
gtgagcagga ggctggagaa cagactggtg ctgctgttct tggcgccgg agcctgccct    240
cagtgccagg ccttcgtgcc catcctgaag gatttctttg tgaggctgac cgacgagttc   300
tacgtgctga gagccgccca gctggccctg tgtatgtga ccaggacag caccgaggag    360
cagcaggacc tgttcctgaa ggacatgccc aagaagtggc tgttcctgcc cttcgaggac   420
gacctgagaa gagacctggg caggcagttc agcgtggaga gactgcccgc cgtggtggtg   480
ctgaagcctg atggcgacgt gctgaccaga gatggcgccg acgagatcca gagactgggc   540
accgcctgct cgccaactg caggaggcc gccgaggtcc tggacagaaa cttccagctg    600
cccgaggatc tggaggatca ggagcccaga tccctgaccg agtgcctgag gcggcacaag   660
tacagagtgg agaaggccgc cagaggcggc agagaccctg gcggcggagg aggagaggag   720
ggcggagccg gcggactgtt ctga                                          744
```

<210> SEQ ID NO 4
<211> LENGTH: 247
<212> TYPE: PRT
<213> ORGANISM: Artificial Sequence
<220> FEATURE:
<223> OTHER INFORMATION: recoded RdCVF1L with Igk signal peptide sequence (+Met)

<400> SEQUENCE: 4

```
Met Glu Thr Asp Thr Leu Leu Leu Trp Val Leu Leu Leu Trp Val Pro
 1               5                  10                  15

Gly Ser Thr Gly Asp Ala Ala Gln Pro Ala Arg Arg Ala Val Arg Ser
             20                  25                  30

Leu Val Pro Met Ala Ser Leu Phe Ser Gly Arg Ile Leu Ile Arg Asn
         35                  40                  45

Asn Ser Asp Gln Asp Glu Leu Asp Thr Glu Ala Glu Val Ser Arg Arg
     50                  55                  60

Leu Glu Asn Arg Leu Val Leu Leu Phe Phe Gly Ala Gly Ala Cys Pro
65                  70                  75                  80

Gln Cys Gln Ala Phe Val Pro Ile Leu Lys Asp Phe Val Arg Leu
                 85                  90                  95

Thr Asp Glu Phe Tyr Val Leu Arg Ala Ala Gln Leu Ala Leu Val Tyr
            100                 105                 110

Val Ser Gln Asp Ser Thr Glu Glu Gln Gln Asp Leu Phe Leu Lys Asp
        115                 120                 125

Met Pro Lys Lys Trp Leu Phe Leu Pro Phe Glu Asp Asp Leu Arg Arg
    130                 135                 140

Asp Leu Gly Arg Gln Phe Ser Val Glu Arg Leu Pro Ala Val Val Val
145                 150                 155                 160
```

-continued

```
Leu Lys Pro Asp Gly Asp Val Leu Thr Arg Asp Gly Ala Asp Glu Ile
                165                 170                 175

Gln Arg Leu Gly Thr Ala Cys Phe Ala Asn Trp Gln Glu Ala Ala Glu
            180                 185                 190

Val Leu Asp Arg Asn Phe Gln Leu Pro Glu Asp Leu Glu Asp Gln Glu
        195                 200                 205

Pro Arg Ser Leu Thr Glu Cys Leu Arg Arg His Lys Tyr Arg Val Glu
    210                 215                 220

Lys Ala Ala Arg Gly Gly Arg Asp Pro Gly Gly Gly Gly Glu Glu
225                 230                 235                 240

Gly Gly Ala Gly Gly Leu Phe
                245

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
ggcggagttg ttacgacat                                                   19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
gggactttcc tacttggca                                                   19

<210> SEQ ID NO 7
<211> LENGTH: 639
<212> TYPE: DNA
<213> ORGANISM: Homo sapiens

<400> SEQUENCE: 7
atggcctccc tgttctctgg ccgcatcctg atccgcaaca atagcgacca ggacgagctg       60
gatacggagg ctgaggtcag tgcaggctg gagaaccggc tggtgctgct gttctttggt       120
gctgggcctt gtccacagtg ccaggccttc gtgcccatcc tcaaggactt cttcgtgcgg      180
ctcacagatg agttctatgt actgcgggcg gctcagctgg ccctggtgta cgtgtcccag      240
gactccacgg aggagcagca ggacctgttc ctcaaggaca tgccaaagaa atggcttttc      300
ctgccctttg aggatgatct gaggagggac ctcgggcgcc agttctcagt ggagcgcctg      360
ccggcggtcg tggtgctcaa gccggacggg gacgtgctca ctcgcgacgg cgccgacgag      420
atccagcgcc tggcaccgc ctgcttcgcc aactggcagg aggcggccga ggtgctggac       480
cgcaacttcc agctgccaga ggacctggag gaccaggagc cacggagcct caccgagtgc      540
ctgcgccgcc acaagtaccg cgtggaaaag gcggcgcgag gcgggcgcga ccccggggga     600
gggggtgggg aggagggcgg ggccgggggg ctgttctga                            639

<210> SEQ ID NO 8
<211> LENGTH: 5035
<212> TYPE: DNA
<213> ORGANISM: Artificial Sequence
<220> FEATURE:
<223> OTHER INFORMATION: expression vector
```

<400> SEQUENCE: 8

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca   120
actccatcac tagggggttcc tgcggccgca cgcgtggagc tagttattaa tagtaatcaa   180
ttacggggtc attagttcat agcccatata tggagttccg cgttacataa cttacggtaa   240
atggcccgcc tggctgaccg cccaacgacc cccgcccatt gacgtcaata atgacgtatg   300
ttcccatagt aacgtcaata gggactttcc attgacgtca atgggtggag tatttacggt   360
aaactgccca cttggcagta catcaagtgt atcatatgcc aagtacgccc cctattgacg   420
tcaatgacgg taaatggccc gcctggcatt atgcccagta catgacctta tgggactttc   480
ctacttggca gtacatctac gtattagtca tcgctattac catggtgatg cggttttggc   540
agtacatcaa tgggcgtgga tagcggtttg actcacgggg atttccaagt ctccacccca   600
ttgacgtcaa tgggagtttg ttttgcacca aaatcaacgg gactttccaa aatgtcgtaa   660
caactccgcc ccattgacgc aaatgggcgg taggcgtgta cggtgggagg tctatataag   720
cagagctcgt ttagtgaacc gtcagatcgc ctggagacgc catccacgct gttttgacct   780
ccatagaaga caccgggacc gatccagcct ccgcggattc gaatcccggc cgggaacggt   840
gcattggaac gcggattccc cgtgccaaga gtgacgtaag taccgcctat agagtctata   900
ggcccacaaa aaatgctttc ttcttttaat atactttttt gtttatctta tttctaatac   960
tttccctaat ctctttcttt cagggcaata atgatacaat gtatcatgcc tctttgcacc  1020
attctaaaga ataacagtga taatttctgg gttaaggcaa tagcaatatt tctgcatata  1080
aatatttctg catataaatt gtaactgatg taagaggttt catattgcta atagcagcta  1140
caatccagct accattctgc ttttatttta tggttgggat aaggctggat tattctgagt  1200
ccaagctagg ccctttttgct aatcatgttc atacctctta tcttcctccc acagctcctg  1260
ggcaacgtgc tggtctgtgt gctggcccat cactttggca aagaattggg attcgaacat  1320
cgattgaatt cgagccacca tgagacagag cacactcctg ctatgggtac tgctgctctg  1380
ggttccaggt tccactggtg acgcggccca gccggccagg cgcgccgtac gaagcttggt  1440
acccgccagc ctgttcagcg gccggatcct gatcaggaac aacagcgacc aggacgagct  1500
ggacaccgag gccgaagtga gcaggaggct ggagaacaga ctggtgctgc tgttctttgg  1560
cgccggagcc tgccctcagt gccaggcctt cgtgcccatc ctgaaggatt ctttgtgcg   1620
gctgaccgac gagttctacg tgctgagagc cgcccagctg gccctggtgt atgtgagcca  1680
ggacagcacc gaggagcagc aggacctgtt cctgaaggac atgcccaaga gtggctgtt   1740
cctgcccttc gaggacgacc tgcggagatg acgagatcta cgggtggcat ccctgtgacc  1800
cctccccagt gcctctcctg gccctggaag ttgccactcc agtgcccacc agccttgtcc  1860
taataaaatt aagttgcatc attttgtctg actaggtgtc cttctataat attatggggt  1920
ggaggggggt ggtatggagc aaggggcaag ttgggaagac aacctgtagg gcctgcgggg  1980
tctattggga accaagctgg agtgcagtgg cacaatcttg gctcactgca atctccgcct  2040
cctgggttca agcgattctc ctgcctcagc ctcccgagtt gttgggattc caggcatgca  2100
tgaccaggct cagctaattt ttgttttttt ggtagagacg gggtttcacc atattggcca  2160
ggctggtctc caactcctaa tctcaggtga tctaccacc ttggcctccc aaattgctgg   2220
gattacaggc gtgaaccact gctcccttcc ctgtccttct gattttgtag gtaaccacgt  2280
```

```
gcggaccgag cggccgcagg aaccccctagt gatggagttg gccactccct ctctgcgcgc    2340
tcgctcgctc actgaggccg ggcgaccaaa ggtcgcccga cgcccgggct ttgcccgggc    2400
ggcctcagtg agcgagcgag cgcgcagctg cctgcagggg cgcctgatgc ggtattttct    2460
ccttacgcat ctgtgcggta tttcacaccg catacgtcaa agcaaccata gtacgcgccc    2520
tgtagcggcg cattaagcgc ggcgggtgtg gtggttacgc gcagcgtgac cgctacactt    2580
gccagcgccc tagcgcccgc tcctttcgct ttcttccctt cctttctcgc cacgttcgcc    2640
ggctttcccc gtcaagctct aaatcggggg ctcccttttag ggttccgatt tagtgcttta    2700
cggcacctcg accccaaaaa acttgatttg ggtgatggtt cacgtagtgg gccatcgccc    2760
tgatagacgg ttttttcgccc tttgacgttg gagtccacgt tctttaatag tggactcttg    2820
ttccaaactg gaacaacact caaccctatc tcgggctatt cttttgattt ataagggatt    2880
ttgccgattt cggcctattg gttaaaaaat gagctgattt aacaaaaatt taacgcgaat    2940
tttaacaaaa tattaacgtt tacaatttta tggtgcactc tcagtacaat ctgctctgat    3000
gccgcatagt taagccagcc ccgacacccg ccaacacccg ctgacgcgcc ctgacgggct    3060
tgtctgctcc cggcatccgc ttacagacaa gctgtgaccg tctccgggag ctgcatgtgt    3120
cagaggtttt caccgtcatc accgaaacgc gcgagacgaa agggcctcgt gatacgccta    3180
tttttatagg ttaatgtcat gataataatg gtttcttaga cgtcaggtgg cacttttcgg    3240
ggaaatgtgc gcggaacccc tatttgttta ttttctaaaa tacattcaaa tatgtatccg    3300
ctcatgagac aataaccctg ataaatgctt caataatatt gaaaaaggaa gagtatgagt    3360
attcaacatt tccgtgtcgc ccttattccc ttttttgcgg cattttgcct tcctgttttt    3420
gctcacccag aaacgctggt gaaagtaaaa gatgctgaag atcagttggg tgcacgagtg    3480
ggttacatcg aactggatct caacagcggt aagatccttg agagttttcg ccccgaagaa    3540
cgttttccaa tgatgagcac ttttaaagtt ctgctatgtg gcgcggtatt atcccgtatt    3600
gacgccgggc aagagcaact cggtcgccgc atacactatt ctcagaatga cttggttgag    3660
tactcaccag tcacagaaaa gcatcttacg gatggcatga cagtaagaga attatgcagt    3720
gctgccataa ccatgagtga taacactgcg gccaacttac ttctgacaac gatcggagga    3780
ccgaaggagc taaccgcttt tttgcacaac atgggggatc atgtaactcg ccttgatcgt    3840
tgggaaccgg agctgaatga agccatacca aacgacgagc gtgacaccac gatgcctgta    3900
gcaatggcaa caacgttgcg caaactatta actggcgaac tacttactct agcttcccgg    3960
caacaattaa tagactggat ggaggcggat aaagttgcag gaccacttct gcgctcggcc    4020
cttccggctg gctggtttat tgctgataaa tctggagccg gtgagcgtgg gtctcgcggt    4080
atcattgcag cactggggcc agatggtaag ccctcccgta tcgtagttat ctacacgacg    4140
gggagtcagg caactatgga tgaacgaaat agacagatcg ctgagatagg tgcctcactg    4200
attaagcatt ggtaactgtc agaccaagtt tactcatata tactttagat tgatttaaaa    4260
cttcattttt aatttaaaag gatctaggtg aagatccttt ttgataatct catgaccaaa    4320
atcccttaac gtgagttttc gttccactga gcgtcagacc ccgtagaaaa gatcaaagga    4380
tcttcttgag atcctttttt tctgcgcgta atctgctgct tgcaaacaaa aaaaccaccg    4440
ctaccagcgg tggtttgttt gccggatcaa gagctaccaa ctctttttcc gaaggtaact    4500
ggcttcagca gagcgcagat accaaatact gtccttctag tgtagccgta gttaggccac    4560
cacttcaaga actctgtagc accgcctaca tacctcgctc tgctaatcct gttaccagtg    4620
gctgctgcca gtggcgataa gtcgtgtctt accgggttgg actcaagacg atagttaccg    4680
```

| | |
|---|---|
| gataaggcgc agcggtcggg ctgaacgggg ggttcgtgca cacagcccag cttggagcga | 4740 |
| acgacctaca ccgaactgag atacctacag cgtgagctat gagaaagcgc cacgcttccc | 4800 |
| gaagggagaa aggcggacag gtatccggta agcggcaggg tcggaacagg agagcgcacg | 4860 |
| agggagcttc caggggggaaa cgcctggtat ctttatagtc ctgtcgggtt tcgccacctc | 4920 |
| tgacttgagc gtcgattttt gtgatgctcg tcagggggggc ggagcctatg gaaaaacgcc | 4980 |
| agcaacgcgg ccttttacg gttcctggcc ttttgctggc cttttgctca catgt | 5035 |

<210> SEQ ID NO 9
<211> LENGTH: 6983
<212> TYPE: DNA
<213> ORGANISM: Artificial Sequence
<220> FEATURE:
<223> OTHER INFORMATION: plasmid

<400> SEQUENCE: 9

| | |
|---|---|
| ctaaattgta agcgttaata ttttgttaaa attcgcgtta aatttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta gggcgaat tggagctcca | 660 |
| ccgcggtggc ggccgctcta gaactagtgg atccccccggg atcccgtagt tattaatagt | 720 |
| aatcaattac ggggtcatta gttcatagcc catatatgga gttccgcgtt acataactta | 780 |
| cggtaaatgg cccgcctggc tgaccgccca acgaccccccg cccattgacg tcaataatga | 840 |
| cgtatgttcc catagtaacg ccaatagggga cttttccattg acgtcaatgg gtggagtatt | 900 |
| tacggtaaac tgcccacttg gcagtacatc aagtgtatca tatgccaagt ccgcccccta | 960 |
| ttgacgtcaa tgacggtaaa tggcccgcct ggcattatgc ccagtacatg accttacggg | 1020 |
| actttcctac ttggcagtac atctacgtat tagtcatcgc tattaccatg gtgatgcggt | 1080 |
| tttggcagta caccaatggg cgtggatagc ggtttgactc acggggattt ccaagtctcc | 1140 |
| accccattga cgtcaatggg agtttgtttt ggcaccaaaa tcaacgggac tttccaaaat | 1200 |
| gtcgtaataa ccccgccccg ttgacgcaaa tgggcggtag gcgtgtacgg tgggaggtct | 1260 |
| atataaacca tatcttcact ctgtacttca gctcgtgtag ctcattagct ccgagctccc | 1320 |
| caacctacag cctgagaggc actggctcgg ttgggtagcc agcctttcgg gtaataaagg | 1380 |
| cttgttggca ttcggcatct acccgtgcct cctgtcttgt cttactcgag cgaacccaca | 1440 |
| actccgtcct gctgagctca cagctcgcgg ggcggtgaag aacacccaac agttggcgcc | 1500 |
| caacgtgggg ctgagtaaga gagactcggc tcgagtaaaa aagacccag ctcgaacgag | 1560 |
| aagactccgg acaggtgagt agttgcgtgt ttccccgggg gtgaagagaa gggagttaga | 1620 |
| aaagaagctt cgtaaggtta gggtgacacc ccaacaggat aaatattata ctatagggaa | 1680 |

```
tcttcaatgg gccattagaa tcacgtgatg catcgataaa taaaaaaaga gggggaatag   1740
ggggccatac accatatgaa atatacctag aatcagaaca taccaaatac caagaccaac   1800
tagaacaaca attttcaaaa caaaaaattg aaaagtggtg ttacgtaagg aacagaagaa   1860
aggaatggaa aggaccctac aaagtgttgt gggacggaga cggggcagca gtaatagagg   1920
agaattcgtg gattcttgta aaggtcccca gctatgggtt tgtggtagta aatgacacag   1980
atacaccacc atccctccgc atccgaaagc ctcgagcagt cggactagca atattcctgc   2040
ttgtgctggc tatcatggcc atcacatcct ccttggtggc agctacaacg ctcgtgaacc   2100
agcacacgac ggctaaggtt gtggagaggg ttgtgcaaaa tgtgtcatat attgctcaaa   2160
cccaggacca attcacccac ctgttcagga atataaacaa cagattaaat gtcctacacc   2220
atagagtttc atacttggag tgtacactta atgggaatga agacccccac ctgtaggttt   2280
ggcaagctag gatcaaggtt aggaacagag agacagcaga atatgggcca aacaggatat   2340
ctgtggtaag cagttcctgc cccggctcag ggccaagaac agttggaaca gcagaatatg   2400
ggccaaacag gatatctgtg gtaagcagtt cctgccccgg ctcagggcca agaacagatg   2460
gtccccagat gcggtcccgc ctcagcagt ttctagagaa ccatcagatg tttccagggt   2520
gccccaagga cctgaaatga ccctgtgcct tatttgaact aaccaatcag ttcgcttctc   2580
gcttctgttc gcgcgcttct gctccccgag ctctatataa gcagagctcg tttagtgaac   2640
cgtcagatcg cctggagacg ccatccacgc tgttttgacc tccatagaag acaccgactc   2700
tagaggatcc accggtcgcc acttaaggcc tgcagctagc gccaccatgg ccagcctgtt   2760
cagcggccgg atcctgattc gcaacaacag cgaccaggac gagctggaca ccgaggccga   2820
ggtgtccagg agactggaga acaggctggt gctgctgttc tttggcgccg agcctgccc   2880 tcagtgccag gccttcgtgc ccatcctgaa ggatttcttt gtgaggctga ccgacgagtt   2940
ctacgtgctg agagccgccc agctggccct ggtgtatgtg agccaggaca gcaccgagga   3000
gcagcaggac ctgttcctga aggacatgcc caagaagtgg ctgttcctgc ccttcgagga   3060
cgacctgaga agagacctgg gcaggcagtt cagcgtggag agactgcccg ccgtggtggt   3120
gctgaagcct gatggcgacg tgctgaccag agatggcgcc gacgagatcc agagactggg   3180
caccgcctgc ttcgccaact ggcaggaggc cgccgaggtc ctggacagaa acttccagct   3240
gcccgaggat ctggaggatc aggagcccag atccctgacc gagtgcctga ggcggcacaa   3300
gtacagagtg gagaaggccg ccagaggcgg cagagaccct ggcggcggag gaggagga   3360 gggcggagcc ggcggactgt tctgatgagc tagcaccggt tgtacaagtc aagcggccaa   3420
ccctccctag atctgttaat caacctctgg attacaaaat ttgtgaaaga ttgactggta   3480
ttcttaacta tgttgctcct tttacgctat gtggatacgc tgctttaatg cctttgtatc   3540
atgctattgc ttcccgtatg gctttcattt tctcctcctt gtataaatcc tggttgctgt   3600
ctctttatga ggagttgtgg cccgttgtca ggcaacgtgg cgtggtgtgc actgtgtttg   3660
ctgacgcaac ccccactggt tggggcattg ccaccacctg tcagctcctt ccgggactt   3720 tcgctttccc cctccctatt gccacggcgg aactcatcgc cgcctgcctt gcccgctgct   3780
ggacaggggc tcggctgttg ggcactgaca attccgtggt gttgtcgggg aagctgacgt   3840
cctttccatg gctgctcgcc tgtgttgcca cctggattct gcgcgggacg tccttctgct   3900
acgtcccttc ggccctcaat ccagcggacc ttccttcccg cggcctgctg ccggctctgc   3960
ggcctcttcc gcgtcttcgc cttcgccctc agacgagtcg gatctccctt tgggccgcct   4020
ccccgcctgt ttcgccttct aggaaactcc tttgggacat cttccgccac gctcctattt   4080
```

-continued

```
taaacttaaa agggtggact gtggggcagg gtgggacctc aggacaacag cagcccccgg    4140
acttcccata tgtgtttatt tgtgaaattt gtgatgctat tgctttattt gtaatctgta    4200
cttcagctcg tgtagctcat tagctccgag ctccccaacc tacagcctga gaggcactgg    4260
ctcggttggg tagccagcct ttcgggtaat aaaggcttgt tggcattcgg catctacccg    4320
tgcctcctgt cttgtcttac tcgagcgaac ccacaactcc gtcctgctga gctcacagct    4380
cgcggggcgg tgaagaacac ccaacagata tatactgtca acatcccatt tggtagctta    4440
tgttctagac aagattctca acaaattctt cccctgaat gtttatttaa aaaaaaaaa     4500
caactactag ggctctgtgc atatgtaagt gagatcctta ttagcaggag aacagcaata    4560
agatattatt acattacaat attatatcct agggtattat aatgcaaggc cattatcaca    4620
tacttggcta acagggtcca tactgttgta atgtattaaa accagactga gtaataaaat    4680
tgacaacaat ataatcatca tctttgttat aggtgggggc attttcaga tgaggtctca    4740
gagcacctgc caagcatgga cctcgagggg gggcccggta cccagctttt gttcccttta    4800
gtgagggtta attgcgcgct tggcgtaatc atggtcatag ctgtttcctg tgtgaaattg    4860
ttatccgctc acaattccac acaacatacg agccgggagc ataaagtgta aagcctgggg    4920
tgcctaatga gtgagctaac tcacattaat tgcgttgcgc tcactgcccg ctttccagtc    4980
gggaaacctg tcgtgccagc tgcattaatg aatcggccaa cgcgcgggga gaggcggttt    5040
gcgtattggg cgctcttccg cttcctcgct cactgactcg ctgcgctcgg tcgttcggct    5100
gcggcgagcg gtatcagctc actcaaaggc ggtaatacgg ttatccacag aatcaggggga    5160
taacgcagga aagaacatgt gagcaaaagg ccagcaaaag gccaggaacc gtaaaaaggc    5220
cgcgttgctg gcgttttttcc ataggctccg ccccctgac gagcatcaca aaaatcgacg    5280
ctcaagtcag aggtggcgaa acccgacagg actataaaga taccaggcgt ttccccctgg    5340
aagctccctc gtgcgctctc ctgttccgac cctgccgctt accggatacc tgtccgcctt    5400
tctcccttcg ggaagcgtgg cgctttctca gctcacgc tgtaggtatc tcagttcggt    5460
gtaggtcgtt cgctccaagc tgggctgtgt gcacgaaccc cccgttcagc ccgaccgctg    5520
cgccttatcc ggtaactatc gtcttgagtc aacccggta agacacgact tatcgccact    5580
ggcagcagcc actggtaaca ggattagcag agcgaggtat gtaggcggtg ctacagagtt    5640
cttgaagtgg tggcctaact acggctacac tagaagaaca gtatttggta tctgcgctct    5700
gctgaagcca gttaccttcg gaaaagagt tggtagctct tgatccggca aacaaaccac    5760
cgctggtagc ggtggttttt ttgtttgcaa gcagcagatt acgcgcagaa aaaaggatc    5820
tcaagaagat cctttgatct tttctacggg gtctgacgct cagtggaacg aaaactcacg    5880
ttaagggatt ttggtcatga gattatcaaa aaggatcttc acctagatcc ttttaaatta    5940
aaaatgaagt tttaaatcaa tctaaagtat atatgagtaa acttggtctg acagttacca    6000
atgcttaatc agtgaggcac ctatctcagc gatctgtcta tttcgttcat ccatagttgc    6060
ctgactcccc gtcgtgtaga taactacgat acgggagggc ttaccatctg gccccagtgc    6120
tgcaatgata ccgcgagacc cacgctcacc ggctccagat ttatcagcaa taaaccagcc    6180
agccggaagg gccgagcgca gaagtggtcc tgcaacttta tccgcctcca tccagtctat    6240
taattgttgc cgggaagcta gagtaagtag ttcgccagtt aatagtttgc gcaacgttgt    6300
tgccattgct acaggcatcg tggtgtcacg ctcgtcgttt ggtatggctt cattcagctc    6360
cggttcccaa cgatcaaggc gagttacatg atccccatg ttgtgcaaaa aagcggttag    6420
```

| | | | | |
|---|---|---|---|---|
| ctccttcggt | cctccgatcg | ttgtcagaag | taagttggcc | gcagtgttat cactcatggt | 6480 |
| tatggcagca | ctgcataatt | ctcttactgt | catgccatcc | gtaagatgct tttctgtgac | 6540 |
| tggtgagtac | tcaaccaagt | cattctgaga | atagtgtatg | cggcgaccga gttgctcttg | 6600 |
| cccggcgtca | atacgggata | ataccgcgcc | acatagcaga | actttaaaag tgctcatcat | 6660 |
| tggaaaacgt | tcttcggggc | gaaaactctc | aaggatctta | ccgctgttga gatccagttc | 6720 |
| gatgtaaccc | actcgtgcac | ccaactgatc | ttcagcatct | tttactttca ccagcgtttc | 6780 |
| tgggtgagca | aaaacaggaa | ggcaaaatgc | cgcaaaaaag | gaataagggg cgacacggaa | 6840 |
| atgttgaata | ctcatactct | tcctttttca | atattattga | agcatttatc agggttattg | 6900 |
| tctcatgagc | ggatacatat | ttgaatgtat | ttagaaaaat | aaacaaatag gggttccgcg | 6960 |
| cacatttccc | cgaaaagtgc | cac | | | 6983 |

<210> SEQ ID NO 10
<211> LENGTH: 5385
<212> TYPE: DNA
<213> ORGANISM: Artificial Sequence
<220> FEATURE:
<223> OTHER INFORMATION: expression vector

<400> SEQUENCE: 10

| | | | | |
|---|---|---|---|---|
| cctgcaggca | gctgcgcgct | cgctcgctca | ctgaggccgc | ccgggcaaag cccgggcgtc | 60 |
| gggcgacctt | tggtcgcccg | gcctcagtga | gcgagcgagc | gcgcagagag ggagtggcca | 120 |
| actccatcac | taggggttcc | tgcggccgca | cgcgtggagc | tagttattaa tagtaatcaa | 180 |
| ttacggggtc | attagttcat | agcccatata | tggagttccg | cgttacataa cttacggtaa | 240 |
| atggcccgcc | tggctgaccg | cccaacgacc | cccgcccatt | gacgtcaata atgacgtatg | 300 |
| ttcccatagt | aacgtcaata | gggactttcc | attgacgtca | atgggtggag tatttacggt | 360 |
| aaactgccca | cttggcagta | catcaagtgt | atcatatgcc | aagtacgccc cctattgacg | 420 |
| tcaatgacgg | taaatggccc | gcctggcatt | atgcccagta | catgacctta tgggactttc | 480 |
| ctacttggca | gtacatctac | gtattagtca | tcgctattac | catggtgatg cggttttggc | 540 |
| agtacatcaa | tgggcgtgga | tagcggtttg | actcacgggg | atttccaagt ctccacccca | 600 |
| ttgacgtcaa | tgggagtttg | ttttgcacca | aaatcaacgg | gactttccaa aatgtcgtaa | 660 |
| caactccgcc | ccattgacgc | aaatgggcgg | taggcgtgta | cggtgggagg tctatataag | 720 |
| cagagctcgt | ttagtgaacc | gtcagatcgc | ctggagacgc | catccacgct gttttgacct | 780 |
| ccatagaaga | caccgggacc | gatccagcct | ccgcggattc | gaatcccggc cgggaacggt | 840 |
| gcattggaac | gcggattccc | cgtgccaaga | gtgacgtaag | taccgcctat agagtctata | 900 |
| ggcccacaaa | aaatgctttc | ttcttttaat | atacttttt | gtttatctta tttctaatac | 960 |
| tttccctaat | ctctttcttt | cagggcaata | atgatacaat | gtatcatgcc tctttgcacc | 1020 |
| attctaaaga | ataacagtga | taatttctgg | gttaaggcaa | tagcaatatt tctgcatata | 1080 |
| aatatttctg | catataaatt | gtaactgatg | taagaggttt | catattgcta atagcagcta | 1140 |
| caatccagct | accattctgc | ttttatttta | tggttgggat | aaggctggat tattctgagt | 1200 |
| ccaagctagg | cccttttgct | aatcatgttc | atacctctta | tcttcctccc acagctcctg | 1260 |
| ggcaacgtgc | tggtctgtgt | gctggcccat | cactttggca | agaattgggg attcgaacat | 1320 |
| cgattgaatt | cgagccacca | tggagacaga | cacactcctg | ctatgggtac tgctgctctg | 1380 |
| ggttccaggt | tccactggtg | acgcggccca | gccggccagg | cgcgccgtac gaagcttggt | 1440 |
| acccgccagc | ctgttcagcg | gccggatcct | gatcaggaac | aacagcgacc aggacgagct | 1500 |

```
ggacaccgag gccgaagtga gcaggaggct ggagaacaga ctggtgctgc tgttctttgg    1560
cgccggagcc tgccctcagt gccaggcctt cgtgcccatc ctgaaggatt tctttgtgag    1620
gctgaccgac gagttctacg tgctgagagc cgcccagctg ccctggtgt atgtgagcca     1680 ggacagcacc gaggagcagc aggacctgtt cctgaaggac atgcccaaga agtggctgtt    1740
cctgcccttc gaggacgacc tgagaagaga cctgggcagg cagttcagcg tggagagact    1800
gcccgccgtg gtggtgctga agcctgatgg cgacgtgctg accagagatg cgccgacga     1860 gatccagaga ctgggcaccg cctgcttcgc caactggcag gaggccgccg aggtcctgga    1920
cagaaacttc cagctgcccg aggatctgga ggatcaggag cccagatccc tgaccgagtg    1980
cctgaggcgg cacaagtaca gagtggagaa ggccgccaga ggcggcagag accctggcgg    2040
cggaggagga gaggagggcg gagccggcgg actgttctga tgagctagca ccggttgtac    2100
aagtcaagcg gccaacccte cctagatcta cgggtggcat ccctgtgacc cctccccagt    2160
gcctctcctg gccctggaag ttgccactcc agtgcccacc agccttgtcc taataaaatt    2220
aagttgcatc attttgtctg actaggtgtc cttctataat attatggggt ggagggggt     2280 ggtatggagc aaggggcaag ttgggaagac aacctgtagg gcctgcgggg tctattggga    2340
accaagctgg agtgcagtgg cacaatcttg gctcactgca atctccgcct cctgggttca    2400
agcgattctc ctgcctcagc ctcccgagtt gttgggattc caggcatgca tgaccaggct    2460
cagctaattt ttgttttttt ggtagagacg gggtttcacc atattggcca ggctggtctc    2520
caactcctaa tctcaggtga tctacccacc ttggcctccc aaattgctgg gattacaggc    2580
gtgaaccact gctcccttcc ctgtccttct gattttgtag gtaaccacgt gcggaccgag    2640
cggccgcagg aaccectagt gatggagttg ccactccct ctctgcgcgc tcgctcgctc    2700
actgaggccg ggcgaccaaa ggtcgcccga cgcccgggct tgcccgggc ggcctcagtg     2760 agcgagcgag cgcgcagctg cctgcagggg cgcctgatgc ggtattttct ccttacgcat    2820
ctgtgcggta tttcacaccg catacgtcaa agcaaccata gtacgcgccc tgtagcggcg    2880
cattaagcgc ggcgggtgtg gtggttacgc gcagcgtgac cgctacactt gccagcgccc    2940
tagcgcccgc tcctttcgct ttcttccctt cctttctcgc cacgttcgcc ggctttcccc    3000
gtcaagctct aaatcggggg ctccctttag ggttccgatt tagtgcttta cggcacctcg    3060
accccaaaaa acttgatttg ggtgatggtt cacgtagtgg gccatcgccc tgatagacgg    3120
tttttcgccc tttgacgttg gagtccacgt tctttaatag tggactcttg ttccaaactg    3180
gaacaacact caaccctatc tcgggctatt cttttgattt ataagggatt ttgccgattt    3240
cggcctattg gttaaaaaat gagctgattt aacaaaaatt taacgcgaat tttaacaaaa    3300
tattaacgtt tacaatttta tggtgcactc tcagtacaat ctgctctgat gccgcatagt    3360
taagccagcc ccgacacccg ccaacacccg ctgacgcgcc ctgacgggct tgtctgctcc    3420
cggcatccgc ttacagacaa gctgtgaccg tctccgggag ctgcatgtgt cagaggtttt    3480
caccgtcatc accgaaacgc gcgagacgaa agggcctcgt gatacgccta ttttttatagg    3540 ttaatgtcat gataataatg gtttcttaga cgtcaggtgg cacttttcgg ggaaatgtgc    3600
gcggaacccc tatttgttta ttttctaaa tacattcaaa tatgtatccg ctcatgagac     3660 ataaccctg ataaatgctt caataatatt gaaaaggaa gagtatgagt attcaacatt      3720
tccgtgtcgc ccttattccc ttttttgcgg cattttgcct tcctgttttt gctcacccag    3780
aaacgctggt gaaagtaaaa gatgctgaag atcagttggg tgcacgagtg ggttacatcg    3840
```

| | |
|---|---|
| aactggatct caacagcggt aagatccttg agagttttcg ccccgaagaa cgttttccaa | 3900 |
| tgatgagcac ttttaaagtt ctgctatgtg gcgcggtatt atcccgtatt gacgccgggc | 3960 |
| aagagcaact cggtcgccgc atacactatt ctcagaatga cttggttgag tactcaccag | 4020 |
| tcacagaaaa gcatcttacg gatggcatga cagtaagaga attatgcagt gctgccataa | 4080 |
| ccatgagtga taacactgcg gccaacttac ttctgacaac gatcggagga ccgaaggagc | 4140 |
| taaccgcttt tttgcacaac atgggggatc atgtaactcg ccttgatcgt tgggaaccgg | 4200 |
| agctgaatga agccatacca aacgacgagc gtgacaccac gatgcctgta gcaatggcaa | 4260 |
| caacgttgcg caaactatta actggcgaac tacttactct agcttcccgg caacaattaa | 4320 |
| tagactggat ggaggcggat aaagttgcag gaccacttct gcgctcggcc cttccggctg | 4380 |
| gctggtttat tgctgataaa tctggagccg gtgagcgtgg gtctcgcggt atcattgcag | 4440 |
| cactggggcc agatggtaag ccctcccgta tcgtagttat ctacacgacg gggagtcagg | 4500 |
| caactatgga tgaacgaaat agacagatcg ctgagatagg tgcctcactg attaagcatt | 4560 |
| ggtaactgtc agaccaagtt tactcatata ctttagat tgatttaaaa cttcattttt | 4620 |
| aatttaaaag gatctaggtg aagatccttt ttgataatct catgaccaaa atcccttaac | 4680 |
| gtgagttttc gttccactga gcgtcagacc ccgtagaaaa gatcaaagga tcttcttgag | 4740 |
| atcctttttt tctgcgcgta atctgctgct tgcaaacaaa aaaaccaccg ctaccagcgg | 4800 |
| tggtttgttt gccggatcaa gagctaccaa ctctttttcc gaaggtaact ggcttcagca | 4860 |
| gagcgcagat accaaatact gtccttctag tgtagccgta gttaggccac cacttcaaga | 4920 |
| actctgtagc accgcctaca tacctcgctc tgctaatcct gttaccagtg gctgctgcca | 4980 |
| gtggcgataa gtcgtgtctt accgggttgg actcaagacg atagttaccg gataaggcgc | 5040 |
| agcggtcggg ctgaacgggg ggttcgtgca cacagcccag cttggagcga acgacctaca | 5100 |
| ccgaactgag atacctacag cgtgagctat gagaaagcgc cacgcttccc gaagggagaa | 5160 |
| aggcggacag gtatccggta agcggcaggg tcggaacagg agagcgcacg agggagcttc | 5220 |
| cagggggaaa cgcctggtat ctttatagtc ctgtcgggtt tcgccacctc tgacttgagc | 5280 |
| gtcgattttt gtgatgctcg tcaggggggc ggagcctatg gaaaaacgcc agcaacgcgg | 5340 |
| cctttttacg gttcctggcc ttttgctggc cttttgctca catgt | 5385 |

<210> SEQ ID NO 11
<211> LENGTH: 2788
<212> TYPE: DNA
<213> ORGANISM: Artificial Sequence
<220> FEATURE:
<223> OTHER INFORMATION: expression vector

<400> SEQUENCE: 11

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc tgcggccgca cgcgtggagc tagttattaa tagtaatcaa | 180 |
| ttacggggtc attagttcat agcccatata tggagttccg cgttacataa cttacggtaa | 240 |
| atggcccgcc tggctgaccg cccaacgacc cccgcccatt gacgtcaata atgacgtatg | 300 |
| ttcccatagt aacgtcaata gggactttcc attgacgtca atgggtggag tatttacggt | 360 |
| aaactgccca cttggcagta catcaagtgt atcatatgcc aagtacgccc cctattgacg | 420 |
| tcaatgacgg taaatggccc gcctggcatt atgcccagta catgacctta tgggactttc | 480 |
| ctacttggca gtacatctac gtattagtca tcgctattac catggtgatg cggttttggc | 540 |

```
agtacatcaa tgggcgtgga tagcggtttg actcacgggg atttccaagt ctccacccca    600
ttgacgtcaa tgggagtttg ttttgcacca aaatcaacgg gactttccaa aatgtcgtaa    660
caactccgcc ccattgacgc aaatgggcgg taggcgtgta cggtgggagg tctatataag    720
cagagctcgt ttagtgaacc gtcagatcgc ctggagacgc catccacgct gttttgacct    780
ccatagaaga caccgggacc gatccagcct ccgcggattc gaatcccggc cgggaacggt    840
gcattggaac gcggattccc cgtgccaaga gtgacgtaag taccgcctat agagtctata    900
ggcccacaaa aaatgctttc ttcttttaat atactttttt gtttatctta tttctaatac    960
tttccctaat ctctttcttt cagggcaata atgatacaat gtatcatgcc tctttgcacc   1020
attctaaaga ataacagtga taatttctgg gttaaggcaa tagcaatatt tctgcatata   1080
aatatttctg catataaatt gtaactgatg taagaggttt catattgcta atagcagcta   1140
caatccagct accattctgc ttttatttta tggttgggat aaggctggat tattctgagt   1200
ccaagctagg ccctttttgct aatcatgttc atacctctta tcttcctccc acagctcctg   1260
ggcaacgtgc tggtctgtgt gctggcccat cactttggca agaattggg attcgaacat   1320
cgattgaatt cgagccacca tggagacaga cacactcctg ctatgggtac tgctgctctg   1380
ggttccaggt tccactggtg acgcggccca gccggccagg cgcgccgtac gaagcttggt   1440
acccgccagc tgttcagcg gccggatcct gatcaggaac aacagcgacc aggacgagct   1500
ggacaccgag gccgaagtga gcaggaggct ggagaacaga ctggtgctgc tgttctttgg   1560
cgccggagcc tgccctcagt gccaggcctt cgtgcccatc ctgaaggatt tctttgtgag   1620
gctgaccgac gagttctacg tgctgagagc cgcccagctg gccctggtgt atgtgagcca   1680
ggacagcacc gaggagcagc aggacctgtt cctgaaggac atgcccaaga gtggctgtt   1740
cctgcccttc gaggacgacc tgaagagaga cctgggcagg cagttcagcg tggagagact   1800
gcccgccgtg gtggtgctga gcctgatgg cgacgtgctg accagagatg cgccgacga   1860
gatccagaga ctgggcaccg cctgcttcgc caactggcag gaggccgccg aggtcctgga   1920
cagaaacttc cagctgcccg aggatctgga ggatcaggag cccagatccc tgaccgagtg   1980
cctgaggcgg cacaagtaca gagtggagaa ggccgccaga ggcggcagag accctggcgg   2040
cggaggagga gaggaggcg gagccggcgg actgttctga tgagctagca ccggttgtac   2100
aagtcaagcg gccaaccctc cctagatcta cgggtggcat ccctgtgacc cctccccagt   2160
gcctctcctg gccctggaag ttgccactcc agtgcccacc agccttgtcc taataaaatt   2220
aagttgcatc attttgtctg actaggtgtc cttctataat attatggggt ggaggggggt   2280
ggtatggagc aaggggcaag ttgggaagac aacctgtagg gcctgcgggg tctattggga   2340
accaagctga agtgcagtgg cacaatcttg gctcactgca atctccgcct cctgggttca   2400
agcgattctc ctgcctcagc ctcccgagtt gttgggattc aggcatgca tgaccaggct   2460
cagctaattt ttgttttttt ggtagagacg gggtttcacc atattggcca ggctggtctc   2520
caactcctaa tctcaggtga tctacccacc ttggcctccc aaattgctgg gattacaggc   2580
gtgaaccact gctcccttcc ctgtccttct gattttgtag gtaaccacgt gcggaccgag   2640
cggccgcagg aaccctagt gatggagttg gccactccct ctctgcgcgc tcgctcgctc   2700
actgaggccg ggcgaccaaa ggtcgcccga cgcccgggct tgcccgggc ggcctcagtg   2760
agcgagcgag cgcgcagctg cctgcagg                                       2788
```

<210> SEQ ID NO 12

<211> LENGTH: 639
<212> TYPE: DNA
<213> ORGANISM: Artificial Sequence
<220> FEATURE:
<223> OTHER INFORMATION: recoded coding region

<400> SEQUENCE: 12

| | | | | | | |
|---|---|---|---|---|---|---|
| atggccagcc | tgttcagcgg | ccggatcctg | atcaggaaca | acagcgacca | ggacgagctg | 60 |
| gacaccgagg | ccgaagtgag | caggaggctg | agaacagac | tggtgctgct | gttctttggc | 120 |
| gccggagcct | ccctcagtg | ccaggccttc | gtgcccatcc | tgaaggattt | ctttgtgagg | 180 |
| ctgaccgaca | gagttctacgt | gctgagagcc | gcccagctgg | ccctggtgta | tgtgagccag | 240 |
| gacagcaccg | aggagcagca | ggacctgttc | ctgaaggaca | tgcccaagaa | gtggctgttc | 300 |
| ctgcccttcg | aggacgacct | gagaagagac | tgggcaggc | agttcagcgt | ggagagactg | 360 |
| cccgccgtgg | tggtgctgaa | gcctgatggc | gacgtgctga | ccagagatgg | cgccgacgag | 420 |
| atccagagac | tgggcaccgc | ctgcttcgcc | aactggcagg | aggccgccga | ggtcctggac | 480 |
| agaaacttcc | agctgcccga | ggatctggag | gatcaggagc | ccagatccct | gaccgagtgc | 540 |
| ctgaggcggc | acaagtacag | agtggagaag | gccgccagag | gcggcagaga | ccctggcggc | 600 |
| ggaggaggag | aggagggcgg | agccggcgga | ctgttctga | | | 639 |

<210> SEQ ID NO 13
<211> LENGTH: 330
<212> TYPE: DNA
<213> ORGANISM: Homo sapiens

<400> SEQUENCE: 13

| | | | | | | |
|---|---|---|---|---|---|---|
| atggcctccc | tgttctctgg | ccgcatcctg | atccgcaaca | atagcgacca | ggacgagctg | 60 |
| gatacggagg | ctgaggtcag | tcgcaggctg | agaaccggc | tggtgctgct | gttctttggt | 120 |
| gctggggctt | gtccacagtg | ccaggccttc | gtgcccatcc | tcaaggactt | cttcgtgcgg | 180 |
| ctcacagatg | agttctatgt | actgcgggcg | gctcagctgg | ccctggtgta | cgtgtcccag | 240 |
| gactccacgg | aggagcagca | ggacctgttc | ctcaaggaca | tgccaaagaa | atggcttttc | 300 |
| ctgccctttg | aggatgatct | gaggaggtga | | | | 330 |

<210> SEQ ID NO 14
<211> LENGTH: 330
<212> TYPE: DNA
<213> ORGANISM: Artificial Sequence
<220> FEATURE:
<223> OTHER INFORMATION: recoded coding region

<400> SEQUENCE: 14

| | | | | | | |
|---|---|---|---|---|---|---|
| atggccagcc | tgttcagcgg | ccggatcctg | atcaggaaca | acagcgacca | ggacgagctg | 60 |
| gacaccgagg | ccgaagtgag | caggaggctg | agaacagac | tggtgctgct | gttctttggc | 120 |
| gccggagcct | ccctcagtg | ccaggccttc | gtgcccatcc | tgaaggattt | ctttgtgcgg | 180 |
| ctgaccgaca | gagttctacgt | gctgagagcc | gcccagctgg | ccctggtgta | tgtgagccag | 240 |
| gacagcaccg | aggagcagca | ggacctgttc | ctgaaggaca | tgcccaagaa | gtggctgttc | 300 |
| ctgcccttcg | aggacgacct | gcggagatga | | | | 330 |

<210> SEQ ID NO 15
<211> LENGTH: 15

```
<212> TYPE: PRT
<213> ORGANISM: Homo sapiens

<400> SEQUENCE: 15

Leu Leu Trp Val Leu Leu Leu Trp Val Pro Gly Ser Thr Gly Asp
1               5                   10                  15
```